United States Patent
Sweet, Jr. et al.

(10) Patent No.: US 11,950,895 B2
(45) Date of Patent: Apr. 9, 2024

(54) RADAR SENSOR SYSTEM FOR BLOOD PRESSURE SENSING, AND ASSOCIATED METHOD

(71) Applicant: Infineon Technologies AG, Newbiberg (DE)

(72) Inventors: Richard S. Sweet, Jr., San Diego, CA (US); Adrian Mikolajczak, Los Altos, CA (US)

(73) Assignee: Infineon Technologies AG, Neubiberg (DE)

( * ) Notice: Subject to any disclaimer, the term of this patent is extended or adjusted under 35 U.S.C. 154(b) by 320 days.

(21) Appl. No.: 17/334,386

(22) Filed: May 28, 2021

(65) Prior Publication Data

US 2022/0378311 A1     Dec. 1, 2022

(51) Int. Cl.
*A61B 5/05*     (2021.01)
*A61B 5/00*     (2006.01)
(Continued)

(52) U.S. Cl.
CPC .............. *A61B 5/05* (2013.01); *A61B 5/0205* (2013.01); *A61B 5/021* (2013.01); *A61B 5/7278* (2013.01);
(Continued)

(58) Field of Classification Search
None
See application file for complete search history.

(56) References Cited

U.S. PATENT DOCUMENTS

| | | | |
|---|---|---|---|
| 2,756,741 | A | 7/1956 | Campanella |
| 3,926,179 | A | 12/1975 | Petzke et al. |

(Continued)

FOREIGN PATENT DOCUMENTS

| | | |
|---|---|---|
| CN | 1463161 A | 12/2003 |
| CN | 1716695 A | 1/2006 |

(Continued)

OTHER PUBLICATIONS

Abuella, Hisham et al., "Non-contact Vital Signs Monitoring through Visible Light Sensing," IEEE Sensors Journal, vol. 20, No. 7, Dec. 14, 2019, 12 pages.

(Continued)

*Primary Examiner* — Devin B Henson
*Assistant Examiner* — Matthew Eric Ogles
(74) *Attorney, Agent, or Firm* — Slater Matsil, LLP

(57) ABSTRACT

In an embodiment, a method includes: generating a displacement signal indicative of a distension of a surface of a skin; determining a temperature of the skin using a temperature sensor; during a calibration time interval, collecting a plurality of distension values from the displacement signal, the plurality of distension values associated with a respective plurality of temperature values determined using the temperature sensor, the plurality of temperature values being indicative of a temperature change of the skin; determining compensation coefficients associated with the plurality of temperature values; and after the calibration time interval, collecting a first distension value from the displacement signal, determining a first temperature value using the temperature sensor, and determining a blood pressure based on the first distension value, the first temperature value, and the determined compensation coefficients.

26 Claims, 8 Drawing Sheets

(51) Int. Cl.
  *A61B 5/0205* (2006.01)
  *A61B 5/021* (2006.01)
  *A61B 5/11* (2006.01)

(52) U.S. Cl.
  CPC ..... *A61B 5/1126* (2013.01); *A61B 2560/0223* (2013.01); *A61B 2562/0271* (2013.01)

(56) References Cited

U.S. PATENT DOCUMENTS

| | | |
|---|---|---|
| 4,241,347 A | 12/1980 | Albanese et al. |
| 4,331,154 A | 5/1982 | Broadwater et al. |
| 6,147,572 A | 11/2000 | Kaminski et al. |
| 6,414,631 B1 | 7/2002 | Fujimoto |
| 6,636,174 B2 | 10/2003 | Arikan et al. |
| 7,048,973 B2 | 5/2006 | Sakamoto et al. |
| 7,057,564 B2 | 6/2006 | Tsai et al. |
| 7,171,052 B2 | 1/2007 | Park |
| 7,179,228 B2 | 2/2007 | Banet |
| 7,317,417 B2 | 1/2008 | Arikan et al. |
| 7,596,241 B2 | 9/2009 | Rittscher et al. |
| 7,692,574 B2 | 4/2010 | Nakagawa |
| 7,873,326 B2 | 1/2011 | Sadr |
| 7,889,147 B2 | 2/2011 | Tam et al. |
| 8,228,382 B2 | 7/2012 | Pattikonda |
| 8,497,805 B2 | 7/2013 | Rofougaran et al. |
| 8,659,369 B2 | 2/2014 | Rofougaran et al. |
| 8,731,502 B2 | 5/2014 | Salle et al. |
| 8,836,596 B2 | 9/2014 | Richards et al. |
| 8,847,814 B2 | 9/2014 | Himmelstoss et al. |
| 8,860,532 B2 | 10/2014 | Gong et al. |
| 8,976,061 B2 | 3/2015 | Chowdhury |
| 9,172,132 B2 | 10/2015 | Kam et al. |
| 9,182,476 B2 | 11/2015 | Wintermantel |
| 9,202,105 B1 | 12/2015 | Wang et al. |
| 9,413,079 B2 | 8/2016 | Kamgaing et al. |
| 9,495,600 B2 | 11/2016 | Heu et al. |
| 9,713,434 B2 | 7/2017 | Barak |
| 9,886,095 B2 | 2/2018 | Pothier |
| 9,935,065 B1 | 4/2018 | Baheti et al. |
| 2003/0036685 A1 | 2/2003 | Goodman |
| 2003/0095263 A1 | 5/2003 | Varshneya et al. |
| 2003/0179127 A1 | 9/2003 | Wienand |
| 2004/0019303 A1* | 1/2004 | Thomson ............ A61B 5/4528 |
| | | 600/595 |
| 2004/0238857 A1 | 12/2004 | Beroz et al. |
| 2005/0261593 A1* | 11/2005 | Zhang ................ A61B 5/02125 |
| | | 600/513 |
| 2006/0001572 A1 | 1/2006 | Gaucher et al. |
| 2006/0005631 A1* | 1/2006 | Hashimoto ............ A61B 5/022 |
| | | 73/780 |
| 2006/0049995 A1 | 3/2006 | Imaoka et al. |
| 2006/0067456 A1 | 3/2006 | Ku et al. |
| 2006/0094937 A1 | 5/2006 | Immoreev et al. |
| 2006/0195035 A1* | 8/2006 | Sun ....................... A61B 5/022 |
| | | 600/503 |
| 2007/0210959 A1 | 9/2007 | Herd et al. |
| 2008/0106460 A1 | 5/2008 | Kurtz et al. |
| 2008/0238759 A1 | 10/2008 | Carocari et al. |
| 2008/0291115 A1 | 11/2008 | Doan et al. |
| 2008/0308917 A1 | 12/2008 | Pressel et al. |
| 2009/0073026 A1 | 3/2009 | Nakagawa |
| 2009/0085815 A1 | 4/2009 | Jakab et al. |
| 2009/0105588 A1* | 4/2009 | Emelianov ........... A61B 5/4869 |
| | | 606/27 |
| 2009/0153428 A1 | 6/2009 | Rofougaran et al. |
| 2009/0315761 A1 | 12/2009 | Walter et al. |
| 2010/0179421 A1 | 7/2010 | Tupin |
| 2010/0207805 A1 | 8/2010 | Haworth |
| 2011/0299433 A1 | 12/2011 | Darabi et al. |
| 2012/0010609 A1 | 1/2012 | Deem et al. |
| 2012/0087230 A1 | 4/2012 | Guo et al. |
| 2012/0092284 A1 | 4/2012 | Rofougaran et al. |
| 2012/0095303 A1* | 4/2012 | He ............................ A61B 5/01 |
| | | 600/301 |
| 2012/0116231 A1 | 5/2012 | Liao et al. |
| 2012/0195161 A1 | 8/2012 | Little et al. |
| 2012/0206339 A1 | 8/2012 | Dahl |
| 2012/0265486 A1 | 10/2012 | Klofer et al. |
| 2012/0268314 A1 | 10/2012 | Kuwahara et al. |
| 2012/0280900 A1 | 11/2012 | Wang et al. |
| 2013/0027240 A1 | 1/2013 | Chowdhury |
| 2013/0106673 A1 | 5/2013 | McCormack et al. |
| 2014/0028542 A1 | 1/2014 | Lovitt et al. |
| 2014/0070994 A1 | 3/2014 | Schmalenberg et al. |
| 2014/0145883 A1 | 5/2014 | Baks et al. |
| 2014/0207252 A1* | 7/2014 | Karr ...................... A61N 1/3605 |
| | | 623/25 |
| 2014/0247136 A1* | 9/2014 | Proud ..................... G08C 17/02 |
| | | 709/224 |
| 2014/0324888 A1 | 10/2014 | Xie et al. |
| 2014/0343393 A1 | 11/2014 | Lee et al. |
| 2015/0018676 A1* | 1/2015 | Barak ...................... G01S 13/88 |
| | | 600/430 |
| 2015/0031967 A1 | 1/2015 | LeBoeuf et al. |
| 2015/0181840 A1 | 7/2015 | Tupin, Jr. et al. |
| 2015/0185316 A1 | 7/2015 | Rao et al. |
| 2015/0212198 A1 | 7/2015 | Nishio et al. |
| 2015/0243575 A1 | 8/2015 | Strothmann et al. |
| 2015/0277569 A1 | 10/2015 | Sprenger et al. |
| 2015/0325925 A1 | 11/2015 | Kamgaing et al. |
| 2015/0346820 A1 | 12/2015 | Poupyrev et al. |
| 2015/0348821 A1 | 12/2015 | Iwanaga et al. |
| 2015/0359436 A1 | 12/2015 | Shim et al. |
| 2015/0364816 A1 | 12/2015 | Murugan et al. |
| 2016/0018511 A1 | 1/2016 | Nayyar et al. |
| 2016/0041617 A1 | 2/2016 | Poupyrev |
| 2016/0041618 A1 | 2/2016 | Poupyrev |
| 2016/0061942 A1 | 3/2016 | Rao et al. |
| 2016/0061947 A1 | 3/2016 | Patole et al. |
| 2016/0098089 A1 | 4/2016 | Poupyrev |
| 2016/0103213 A1 | 4/2016 | Ikram et al. |
| 2016/0109566 A1 | 4/2016 | Liu et al. |
| 2016/0118353 A1 | 4/2016 | Ahrens et al. |
| 2016/0135655 A1 | 5/2016 | Ahn et al. |
| 2016/0146931 A1 | 5/2016 | Rao et al. |
| 2016/0146933 A1 | 5/2016 | Rao et al. |
| 2016/0178730 A1 | 6/2016 | Trotta et al. |
| 2016/0187462 A1 | 6/2016 | Altus et al. |
| 2016/0191232 A1 | 6/2016 | Subburaj et al. |
| 2016/0200276 A1* | 7/2016 | Diewald ................. G01S 13/04 |
| | | 342/28 |
| 2016/0223651 A1 | 8/2016 | Kamo et al. |
| 2016/0240907 A1 | 8/2016 | Haroun |
| 2016/0249133 A1 | 8/2016 | Sorensen |
| 2016/0252607 A1 | 9/2016 | Saboo et al. |
| 2016/0259037 A1 | 9/2016 | Molchanov et al. |
| 2016/0266233 A1 | 9/2016 | Mansour |
| 2016/0269815 A1 | 9/2016 | Liao et al. |
| 2016/0291130 A1 | 10/2016 | Ginsburg et al. |
| 2016/0299215 A1 | 10/2016 | Dandu et al. |
| 2016/0306034 A1 | 10/2016 | Trotta et al. |
| 2016/0320852 A1 | 11/2016 | Poupyrev |
| 2016/0320853 A1 | 11/2016 | Lien et al. |
| 2016/0327633 A1 | 11/2016 | Kumar Y.B. et al. |
| 2016/0334502 A1 | 11/2016 | Ali et al. |
| 2016/0349845 A1 | 12/2016 | Poupyrev et al. |
| 2017/0033062 A1 | 2/2017 | Liu et al. |
| 2017/0045607 A1 | 2/2017 | Bharadwaj et al. |
| 2017/0052618 A1 | 2/2017 | Lee et al. |
| 2017/0054449 A1 | 2/2017 | Mani et al. |
| 2017/0060254 A1 | 3/2017 | Molchanov et al. |
| 2017/0065184 A1 | 3/2017 | Barak |
| 2017/0070952 A1 | 3/2017 | Balakrishnan et al. |
| 2017/0074974 A1 | 3/2017 | Rao et al. |
| 2017/0074980 A1 | 3/2017 | Adib et al. |
| 2017/0090014 A1 | 3/2017 | Subburaj et al. |
| 2017/0090015 A1 | 3/2017 | Breen et al. |
| 2017/0115377 A1 | 4/2017 | Giannini et al. |
| 2017/0119318 A1 | 5/2017 | Shay et al. |
| 2017/0131395 A1 | 5/2017 | Reynolds et al. |
| 2017/0139036 A1 | 5/2017 | Nayyar et al. |
| 2017/0141453 A1 | 5/2017 | Waelde et al. |
| 2017/0170947 A1 | 6/2017 | Yang |

(56) References Cited

U.S. PATENT DOCUMENTS

| | | | |
|---|---|---|---|
| 2017/0172493 A1* | 6/2017 | Rahman | A61B 5/742 |
| 2017/0176574 A1 | 6/2017 | Eswaran et al. | |
| 2017/0192847 A1 | 7/2017 | Rao et al. | |
| 2017/0201019 A1 | 7/2017 | Trotta | |
| 2017/0212597 A1 | 7/2017 | Mishra | |
| 2017/0364160 A1 | 12/2017 | Malysa et al. | |
| 2018/0046255 A1 | 2/2018 | Rothera et al. | |
| 2018/0071473 A1 | 3/2018 | Trotta et al. | |
| 2018/0101239 A1 | 4/2018 | Yin et al. | |
| 2019/0053739 A1* | 2/2019 | Inoue | G06Q 40/02 |
| 2019/0178764 A1* | 6/2019 | Pelssers | A61B 5/442 |
| 2019/0282106 A1* | 9/2019 | Shay | A61B 5/681 |
| 2021/0055386 A1* | 2/2021 | Rimini | H04B 7/0426 |
| 2021/0123872 A1 | 8/2021 | Shaker | |
| 2021/0249769 A1* | 8/2021 | Diewald | G01S 7/023 |

FOREIGN PATENT DOCUMENTS

| | | |
|---|---|---|
| CN | 101490578 A | 7/2009 |
| CN | 101585361 A | 11/2009 |
| CN | 102788969 A | 11/2012 |
| CN | 102967854 A | 3/2013 |
| CN | 103529444 A | 1/2014 |
| CN | 203950036 U | 11/2014 |
| DE | 102008054570 A1 | 6/2010 |
| DE | 102011100907 A1 | 1/2012 |
| DE | 102011075725 A1 | 11/2012 |
| DE | 102014118063 A1 | 7/2015 |
| GB | 2247799 A | 3/1992 |
| JP | 2001174539 A | 6/2001 |
| JP | 2004198312 A | 7/2004 |
| JP | 2006234513 A | 9/2006 |
| JP | 2008029025 A | 2/2008 |
| JP | 2008089614 A | 4/2008 |
| JP | 2009069124 A | 4/2009 |
| JP | 2011529181 A | 12/2011 |
| JP | 2012112861 A | 6/2012 |
| JP | 2013521508 A | 6/2013 |
| JP | 2014055957 A | 3/2014 |
| KR | 20090063166 A | 6/2009 |
| KR | 20140082815 A | 7/2014 |
| WO | 2007060069 A1 | 5/2007 |
| WO | 2013009473 A2 | 1/2013 |
| WO | 2016033361 A1 | 3/2016 |
| WO | 2020041715 A1 | 2/2020 |

OTHER PUBLICATIONS

Alizadeh, Mostafa et al., "Remote Monitoring of Human Vital Signs Using mm-Wave FMCW Radar," IEEE Access, May 6, 2019, 11 pages.

Ballinger, Brandon et al., "DeepHeart: Semi-Supervised Sequence Learning for Cardiovascular Risk Prediction," The Thirty-Second AAAI Conference on Artificial Intelligence (AAAI-18), Apr. 26, 2018, 8 pages.

"BT24MTR11 Using BGT24MTR11 in Low Power Applications 24 GHZ Rader," Application Note AN341, Revision: Rev 1.0, Infineon Technologies AG, Munich, Germany, Dec. 2, 2013, 25 pages.

Blazejczyk, K. et al., "Influence of Solar Radiation on Skin Temperature in Standing and Walking Subjects Outdoors," 1998, 4 pages.

Block, Robert C. et al., "Conventional pulse transit times as markers of blood pressure changes in humans," Scientific Reports Natureresearch, Oct. 2, 2020, 9 pages.

Blumio, "A Scientific Approach to Cuffless Blood Pressure Monitoring," https://www.blumio.com/science/, Mar. 16, 2021, 6 pages.

Carek, Andrew M. et al., "SeismoWatch: Wearable Cuffless Blood Pressure Monitoring Using Pulse Transit Time," Department fo Health & Human Services USA, HHS Public Access, Dec. 13, 2018, 24 pages.

Chen, Xiaolong et al., "Detection and Extraction of Marine Target with Micromotion via Short-Time Fractional Fourier Transform in Sparse Domain," IEEE International Conference on Signal Processing, Communications and Computing, CSPCC, Aug. 5-8, 2016, 5 pages.

Chen, Xiaolong et al., "Detection and Extraction of Target with Micromotion in Spiky Sea Clutter via Short-Time Fractional Fourier Transform", IEEE Transactions on Geoscience and Remote Sensing, vol. 52, No. 2, Feb. 2014, 17 pages.

Chioukh, Lydia et al., "Noise and Sensitivity of Harmonic Radar Architecture for Remote Sensing and Detection of Vital Signs", IEEE Transactions on Microwave Theory and Techniques, vol. 62, No. 9, Sep. 2014, 9 pages.

Chuanhua, Du, "FMCW Radar Range-Doppler Processing and Beam Formation Technology," Chinese Doctoral Dissertations & Master's Theses Full Text Database (Masters)—Information Science and Technology Series, China National Knowledge Infrastructure, ISSN 1674-0246, CN 11-9144/G, Dec. 16, 2004-Mar. 2015, 14 pages.

Deacon, Peter et al., "Frequency Modulated Continuous Wave (FMCW) Radar," Design Team 6 Technical Lecture, Nov. 9, 2011, 27 pages.

Dham, Vivek "Programming Chirp Parameters in TI Radar Devices," Application Report SWRA553, Texas Instruments, May 2017, 15 pages.

Diederichs, Kailtyn et al., "Wireless Biometric Individual Identification Utilizing Millimeter Waves", IEEE Sensors Letters, vol. 1, No. 1, IEEE Sensors Council 3500104, Feb. 2017, 4 pages.

Dooring Alert Systems, "Riders Matter," http:\\dooringalertsystems.com, printed Oct. 4, 2017, 16 pages.

Emilio, Maurizio Di Paolo, "Radar-Based Blood Pressure Sensors on the Way," EE Times, https://www.eetimes.com/radar-based-blood-pressure-sensors-on-the-way/#, Jul. 23, 2020, 4 pages.

Filippelli, Mario et al., "Respiratory dynamics during laughter," J Appl Physiol, (90), Apr. 2001, http://jap.physiology.org/content/jap/90/4/1441.full.pdf., 6 pages.

Fox, Ben, "The Simple Technique That Could Save Cyclists' Lives, " https://www.outsideonline.com/2115116/simple-technique-could-save-cyclists-lives, Sep. 19, 2016, 6 pages.

Gigie, Andrew et al., "Novel Approach for Vibration Detection Using Indented Radar", Progess in Electromagnetic Research C, vol. 87, Oct. 4, 2018, 16 pages.

Gouveia, Carolina et al., "A Review on Methods for Random Motion Detection and Compensation in Bio-Radar Systems", Sensors, MDPI, Jan. 31, 2019, 17 pages.

Gu, Changzhan et al., "Assessment of Human Respiration Patterns via Noncontact Sensing Using Doppler Multi-Radar System", Sensors Mar. 2015, 15(3), doi: 10.3390/s150306383, 17 pages.

Gu, Changzhan et al., "Deep Neural Network based Body Movement Cancellation for Doppler Radar Vital Sign Detection", IEEE MTT-S International Wireless Symposium (IWS) May 19-22, 2019, 3 pages.

Gu, Changzhu "Short-Range Noncontact Sensors for Healthcare and Other Emerginng Applications: A Review", Sensors, MDPI, Jul. 26, 2016, 24 pages.

Gu, Changzhan et al., "From Tumor Targeting to Speed Monitoring", IEEE Microwave Magazine, ResearchGate, Jun. 2014, 11 pages.

Guercan, Yalin "Super-resolution Algorithms for Joint Range-Azimuth-Doppler Estimation in Automotive Radars," Technische Universitet Delft, TUDelft University of Technology Challenge the Future, Jan. 25, 2017, 72 pages.

Hu, Wei et al., "Noncontact Accurate Measurement of Cardiopulmonary Activity Using a Compact Quadrature Doppler Radar Sensor", IEEE Transactions on Biomedical Engineering, vol. 61, No. 3, Mar. 2014, 11 pages.

Immoreev, I. Ya. "Ultrawideband Radars: Features and Capabilities", Journal of Communications Technology and Electronics, ISSN: 1064-2269, vol. 54, No. 1, Feb. 8, 2009, 26 pages.

Inac, Ozgur et al., "A Phased Array RFIC with Built-In Self-Test Capabilities," IEEE Transactions on Microwave Theory and Techniques, vol. 60, No. 1, Jan. 2012, 10 pages.

Infineon, "Health effects of mmWave radiation," www.infineon.com, Nov. 2018, 2 pages.

(56) References Cited

OTHER PUBLICATIONS

Johnson, Jessi E. et al., "Wearable Millimeter-Wave Device for Contactless Measurement of Arterial Pulses," IEEE Transactions on Biomedical Circuits and Systems, vol. 13, No. 6, Dec. 2019, 10 pages.
Johnson, Jessi et al., "Arterial Pulse Measurement with Wearable Millimeter Wave Device," 2019 IEEE 16th International Conference on Wearable and Implantable Body Sensor Networks (BSN), Jul. 25, 2019, 4 pages.
Khamdaeng, T. et al. "Arterial stiffness identification of the human carotid artery using the stress-strain relationship In vivo," National Institute of Health, NIH Public Access, May 5, 2014, 33 pages.
Killedar, Abdulraheem "XWR1xxx Power Management Optimizations—Low Cost LC Filter Solution," Application Report SWRA577, Texas Instruments, Oct. 2017, 19 pages.
Kishore, N. et al., "Millimeter Wave Antenna for Intelligent Transportation Systems Application", Journal of Microwaves, Optoelectronics and Electromagnetic Applications, vol. 17, No. 1, Mar. 2018, 8 pages.
Kizhakkel, V., "Pulsed Radar Target Recognition Based on Micro-Doppler Signatures Using Wavelet Analysis", A Thesis, Graduate Program in Electrical and Computer Engineering, Ohio State University, Jan. 2013-May 2013, 118 pages.
Kuehnke, Lutz, "Phased Array Calibration Procedures Based on Measured Element Patterns," 2001 Eleventh International Conference on Antennas and Propagation, IEEE Conf., Publ. No. 480, Apr. 17-20, 2001, 4 pages.
Li, Changzhi et al., "A Review on Recent Advances in Doppler Radar Sensors for Noncontact Healthcare Monitoring", IEEE Transactions on Microwave Theory and Techniques, vol. 61, No. 5, May 2013, 15 pages.
Li, Changzhi et al., "A Review on Recent Progress of Portable Short-Range Noncontact Microwave Radar Systems", IEEE Transactions on Microwave Theory and Techniques, vol. 65, No. 5, May 2017, 15 pages.
Li, Changzhi et al., "Random Body Movement Cancellation in Doppler Radar Vital Sign Detection", IEEE Transactions on Microwave Theory and Techniques, vol. 56, No. 12, Dec. 2008, 11 pages.
Li, Changzhi et al., "Robust Overnight Monitoring of Human Vital Signs by a Non-contact Respiration and Heartbeat Detector", IEEE Proceedings of the 28th EMBS Annual International Conference, FrA05.5, Aug. 30-Sep. 3, 2006, 4 pages.
Li, Changzhi "Vital-sign monitoring on the go", Sensors news and views, www.nature.com/naturelectronics, Nature Electronics, vol. 2, Jun. 2019, 2 pages.
Li, Chunhui et al., "Determining elastic properties of skin by measuring surface waves from an impulse mechanical stimulus using phase-sensitive optical coherence tomography," Journal of the Royal Society Interface, Nov. 2, 2011, 11 pages.
Lim, Soo-Chul et al., "Expansion of Smartwatch Touch Interface from Touchscreen to Around Device Interface Using Infrared Line Image Sensors," Sensors 2015, ISSN 1424-8220, vol. 15, 16642-16653, doi: 10.3390/s150716642, www. mdpi.com/journal/sensors, Jul. 15, 2009, 12 pages.
Lin, Jau-Jr et al., "Design of an FMCW radar baseband signal processing system for automotive application," SpringerPlus a SpringerOpen Journal, (2016) 5:42, http://creativecommons.org/licenses/by/4.0/, DOI 10.1186/s40064-015-1583-5; Jan. 2016, 16 pages.
Massagram, Wansuree et al., "Assessment of Heart Rate Variability and Respiratory Sinus Arrhythmia via Doppler Radar", IEEE Transactions on Microwave Theory and Techniques, vol. 57, No. 10, Oct. 2009, 8 pages.
Mercuri, Marco et al., "Vital-sign monitoring and spatial tracking of multiple people using a contactless radar-based sensor", Nature Electronics, vol. 2, Articles, https://doi.org/10.1038/s41928-019-0258-6, Jun. 2019, 13 pages.

Microwave Journal Frequency Matters, "Single-Chip 24 GHz Radar Front End," Infineon Technologies AG, www.microwavejournal.com/articles/print/21553-single-chip-24-ghz-radar-front-end, Feb. 13, 2014, 2 pages.
Mostov, K., et al., "Medical applications of shortwave FM radar: Remote monitoring of cardiac and respiratory motion", Am. Assoc. Phys. Med., 37(3), Mar. 2010, 7 pages.
Oguntala, G. et al., "Indoor location identification technologies for real-time IoT-based applications: an inclusive survey", Elsevier Inc., http:/hdl.handle.net/10454/16634, Oct. 2018, 42 pages.
Peng, Zhengyu et al., "A Portable FMCW Interferometry Radar with Programmable Low-IF Architecture for Localization, ISAR Imaging, and Vial Sign Tracking", IEEE Transactions on Microwave Theory and Techniques, Dec. 15, 2016, 11 pages.
Qadir, Shahida G., et al., "Focused ISAR Imaging of Rotating Target in Far-Field Compact Range Anechoic Chamber," 14th International Conference on Aerospace Sciences & Aviation Technology, ASAT-14-241-IP, May 24-26, 2011, 7 pages.
Richards, Mark A., "Fundamentals of Radar Signal Processing," McGraw Hill Electronic Engineering, ISBN: 0-07-144474-2, Jun. 2005, 93 pages.
Sakamoto, Takuya et al., "Feature-Based Correlation and Topological Similarity for Interbeat Interval Estimation Using Ultrawideband Radar", IEEE Transactions on Biomedical Engineering, vol. 63, No. 4, Apr. 2016, 11 pages.
Santra, Avik et al., "Short-range multi-mode continuous-wave radar for vital sign measurement and imaging", ResearchGate, Conference Paper, Apr. 2018, 6 pages.
Schellenberger, Sven et al., "A dataset of clinically recorded radar vital signs with synchronised reference sensor signals," Scientific Data, https://www.nature.com/articles/s41597-020-00629-5, Sep. 8, 2020, 27 pages.
Schellenberger, Sven et al., "Continuous In-Bed Monitoring of Vital Signs Using a Multi Radar Setup for Freely Moving Patients," Sensors, MDPI, Oct. 15, 2020, 14 pages.
Schroff, Florian et al., "FaceNet: A Unified Embedding for Face Recognition and Clustering," CVF, CVPR2015, IEEE Computer Society Conference on Computer Vision and Pattern Recognition; Mar. 12, 2015, 9 pages.
Simon, W., et al., "Highly Integrated KA-Band Tx Frontend Module Including 8x8 Antenna Array," IMST GmbH, Germany, Asia Pacific Microwave Conference, Dec. 7-10, 2009, 63 pages.
Singh, Aditya et al., "Data-Based Quadrature Imbalance Compensation for a CW Doppler Radar System", https://www.researchgate.net/publication/258793573, IEEE Transactions on Microwave Theory and Techniques, Apr. 2013, pages.
Solá, Josep et al., "The Handbook of Cuffless Blood Pressure Monitoring," Springer, 2019, 245 pages.
Subramani, Srinivasan, "Using mmWave radar for vital signs monitoring," https://www.embedded.com/using-mmwave-radar-for-vital-signs-monitoring/, Aug. 17, 2020, 12 pages.
Suleymanov, Suleyman, "Design and Implementation of an FMCW Radar Signal Processing Module for Automotive Applications," Master Thesis, University of Twente, Aug. 31, 2016, 64 pages.
Thayaparan, T. et al., "Micro-Doppler Radar Signatures for Intelligent Target Recognition," Defence Research and Development Canada, Technical Memorandum, DRDC Ottawa TM 2004-170, Sep. 2004, 73 pages.
Thayaparan, T. et al., "Intelligent target recognition using micro-Doppler radar signatures," Defence R&D Canada, Radar Sensor Technology III, Proc. of SPIE, vol. 7308, 730817, Dec. 9, 2009, 11 pages.
Tu, Jianxuan et al., "Fast Acquisition of Heart Rate in Noncontact Vital Sign Radar Measurement Using Time-Window-Variation Technique", IEEE Transactions on Instrumentation and Measurement, vol. 65, No. 1, Jan. 2016, 11 pages.
Vinci, Gabor et al., "Microwave Interferometer Radar-Based Vital Sign Detection for Driver Monitoring Systems", IEEE MTT-S International Conference on Microwaves for Intelligent Mobility, Apr. 27-29, 2015, 4 pages.

(56) References Cited

OTHER PUBLICATIONS

Vinci, Gabor et al., "Six-Port Radar Sensor for Remote Respiration Rate and Heartbeat Vital-Sign Monitoring", IEEE Transactions on Microwave Theory and Techniques, vol. 61, No. 5, May 2013, 8 pages.

Wang, Fu-Kang et al., "Wrist Pulse Rate Monitor Using Self-Injection-Locked Radar Technology", Biosensors, MDPI, Oct. 26, 2016, 12 pages.

Wang, Guochao et al., "Application of Linear-Frequency-Modulated Continuous-Wave (LFMCW) Radars for Tracking of Vital Signs," IEEE Transactions on Microwave Theory and Techniques, vol. 62, No. 6, May 5, 2014, 14 pages.

Wikipedia, "Blood pressure," https://en.wikipedia.org/wiki/Blood_pressure, Mar. 16, 2021, 20 pages.

Wikipedia, "Continuous noninvasive arterial pressure," https://en.wikipedia.org/wiki/Continuous_noninvasive_arterial_pressure, Mar. 16, 2021, 9 pages.

Wikipedia, "Young's modulus, " https://en.wikipedia.org/wiki/Young%27s_modulus, Apr. 13, 2021, 12 pages.

Wilder, Carol N., et al., "Respiratory patterns in infant cry," Canada Journal of Speech, Human Communication Winter, 1974-75, http://cjslpa.ca/files/1974_HumComm_Vol_01/No_03_2-60/Wilder_Baken_HumComm_1974.pdf, 17 pages.

Will, Christoph et al., "Advanced Template Matching Algorithm for Instantaneous Heartbeat Detection using Continuous Wave Radar Systems", ResearchGate, May 2017, 5 pages.

Will, Christoph et al., "Human Target Detection, Tracking, and Classification Using 24-GHz FMCW Radar", IEEE Sensors Journal, vol. 19, No. 17, Sep. 1, 2019, 17 pages.

Will, Christoph et al., "Local Pulse Wave Detection using Continuous Wave Radar Systems", IEEE Journal of Electromagnetics, RF and Microwaves in Medicine and Biology, Oct. 25, 2017, 9 pages.

Will, Christoph et al., "Radar-Based Heart Sound Detection", Scientific Reports, www.nature.com/scientificreports, Jul. 26, 2018, 15 pages.

Kin, Qin et al., "Signal Processing for Digital Beamforming FMCW SAR," Hindawi Publishing Corporation, Mathematical Problems in Engineering, vol. 2014, Article ID 859890, http://dx.doi.org/10.1155/2014/859890, Apr. 15, 2014, 11 pages.

* cited by examiner

RADAR SENSOR SYSTEM FOR BLOOD PRESSURE SENSING, AND ASSOCIATED METHOD

TECHNICAL FIELD

The present disclosure relates generally to an electronic system and method, and, in particular embodiments, to a radar sensor system for blood pressure sensing system, and associated method.

BACKGROUND

Blood pressure, also referred to as arterial pressure, is one of the vital signs that healthcare professionals monitor when evaluating the health of a patient. Blood pressure is often expressed in terms of systolic pressure and diastolic pressure. The systolic pressure may be understood as the pressure that circulating blood exerts on the walls of the blood vessels at the point of maximum contraction of the heart. The diastolic pressure may be understood as the pressure that circulating blood exerts on the walls of the blood vessels at the point of maximum expansion of the heart (e.g., when the blood in the blood vessel is static). The systolic pressure may be referred to as the maximum or peak pressure while the diastolic pressure may be referred to as the baseline pressure.

Blood pressure may be measured using non-invasive tonometry methods that involve the application of a force to a superficial artery to sense its pulsatility. Examples of tonometry methods include an auscultatory method (e.g., using Korotkoff sounds), oscillometric method (e.g., based on the envelope of the oscillation of cuff pressure during cuff deflation), pulse wave velocity (PWV) method (e.g., based on the velocity of a pulse traveling through the blood vessel), and pulse transit time (PTT) method (e.g., based on the time it takes a pulse to travel a known distance). Blood pressure may also be measured using pulse tonometry (e.g., by applying a counter pressure to measure arterial distension) and using vascular unloading (e.g., by measuring counter pressure required to maintain a constant blood volume).

For example, blood pressure can be measured non-invasively using an auscultatory method by using a sphygmomanometer, which uses an inflatable cuff and a sensor (e.g., a stethoscope). For example, starting with the inflatable cuff exerting a pressure (e.g., on the arm) that is higher than the systolic pressure, the cuff is gradually deflated until the medical practitioner (or a sensor) detects a first Korotkoff sound (e.g., an audible tap). The pressure exerted by the cuff when the first Korotkoff sound is detected corresponds to the systolic pressure (which is the threshold pressure in which blood is allowed to flow through the blood vessel). As the pressure continues to gradually lower, a last Korotkoff sound is detected before the blood is no longer restricted by the pressure exerted by the cuff. The pressure exerted by the cuff when the last Korotkoff sound is detected corresponds to the diastolic pressure.

As another example, blood pressure may also be measured in a continuous and non-invasive manner using a continuous noninvasive arterial pressure (CNAP) method, which a vascular unloading method. For example, a CNAP module uses a double finger cuff with an infrared (IR) sensor and air chambers. The IR sensor is used to measure the blood volume. A control system is used to control the pressure that the air chambers exert onto the fingers to keep the blood volume constant. The blood pressure is derived from the pressure exerted by the air chambers to keep the blood volume constant (since the counter pressured applied by the air chambers onto the fingers is as high as the pressure inside the blood vessel to cause a constant blood volume).

FIG. 1 shows exemplary blood pressure waveform 100, as measured using the CNAP method. As shown, the CNAP method generates a continuous waveform that includes the systolic pressure $P_{SBP}$ and the diastolic pressure $P_{DBP}$.

SUMMARY

In accordance with an embodiment, a method includes: generating a displacement signal indicative of a distension of a surface of a skin; determining a temperature of the skin using a temperature sensor; during a calibration time interval, collecting a plurality of distension values from the displacement signal, the plurality of distension values associated with a respective plurality of temperature values determined using the temperature sensor, the plurality of temperature values being indicative of a temperature change of the skin; determining compensation coefficients associated with the plurality of temperature values; and after the calibration time interval, collecting a first distension value from the displacement signal, determining a first temperature value using the temperature sensor, and determining a blood pressure based on the first distension value, the first temperature value, and the determined compensation coefficients.

In accordance with an embodiment, a method includes: transmitting a plurality of radar signals towards a surface of a skin using a millimeter-wave radar; receiving a plurality of reflected radar signals using the millimeter-wave radar; using the millimeter-wave radar, generating a displacement signal indicative of a distension of the surface of the skin based on the reflected radar signals, the skin covering a blood vessel; determining a temperature of the skin using a temperature sensor; during a calibration time interval, applying electromagnetic energy to the skin using the millimeter-wave radar to cause an increase in temperature of the skin, collecting a plurality of distension values from the displacement signal, the plurality of distension values associated with a respective plurality of temperature values determined using the temperature sensor, the plurality of temperature values indicative of the temperature increase of the skin caused by the applied electromagnetic energy, and determining compensation coefficients associated with the plurality of temperature values; and after the calibration time interval, collecting a first distension value from the displacement signal, determining a first temperature value using the temperature sensor, and determining a blood pressure based on the first distension value, the first temperature value, and the determined compensation coefficients.

In accordance with an embodiment, a wearable device includes: a millimeter-wave radar configured to: transmit a plurality of a plurality of radar signals towards a surface of a skin, receive a plurality of reflected radar signals, and generate a displacement signal indicative of a distension of the surface of the skin based on the reflected radar signals; a temperature sensor configured to measure temperature indicative of a temperature of the surface of the skin; and a controller configured to: during a calibration time interval, cause the millimeter-wave radar to apply electromagnetic energy to the skin to cause an increase in temperature of the skin, collect a plurality of distension values from the displacement signal, the plurality of distension values associated with a respective plurality of temperature values determined using the temperature sensor, the plurality of temperature values indicative of the temperature increase of the skin caused by the applied electromagnetic energy, and determine compensation coefficients associated with the plurality of temperature values, and after the calibration time interval, collect a first distension value from the displacement signal, determine a first temperature value using the temperature sensor, and determine a blood pressure based on the first distension value, the first temperature value, and the determined compensation coefficients.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale.

DETAILED DESCRIPTION OF ILLUSTRATIVE EMBODIMENTS

Figure 1:
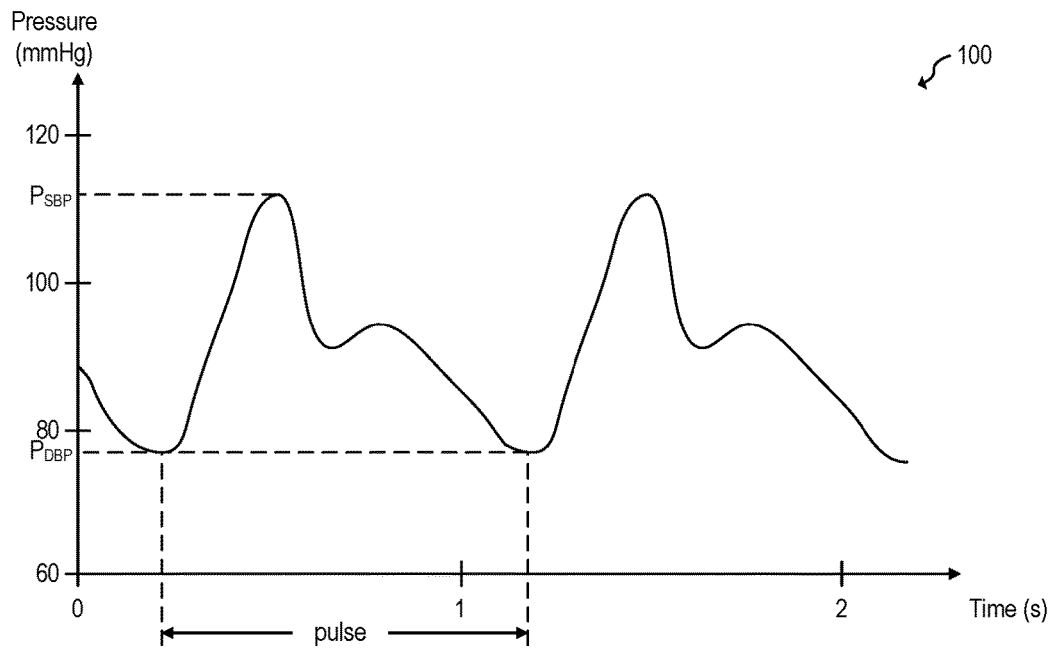
FIG. 1 shows an exemplary blood pressure waveform, as measured using the CNAP method.

The making and using of the embodiments disclosed are discussed in detail below. It should be appreciated, however, that the present invention provides many applicable inventive concepts that can be embodied in a wide variety of specific contexts. The specific embodiments discussed are merely illustrative of specific ways to make and use the invention, and do not limit the scope of the invention.

The description below illustrates the various specific details to provide an in-depth understanding of several example embodiments according to the description. The embodiments may be obtained without one or more of the specific details, or with other methods, components, materials and the like. In other cases, known structures, materials or operations are not shown or described in detail so as not to obscure the different aspects of the embodiments. References to "an embodiment" in this description indicate that a particular configuration, structure or feature described in relation to the embodiment is included in at least one embodiment. Consequently, phrases such as "in one embodiment" that may appear at different points of the present description do not necessarily refer exactly to the same embodiment. Furthermore, specific formations, structures or features may be combined in any appropriate manner in one or more embodiments.

Embodiments of the present invention will be described in a specific context, a mobile wearable device (e.g., watch, wrist band) for blood pressure sensing of a human using a millimeter-wave radar and a temperature sensor, and associated calibration method and method of use. Embodiments of the present invention may be used in other types of devices, such as vital sign monitors. Some embodiments may operate in regimes different than millimeter-wave. Some embodiments may use other sensors, instead of or in addition to the millimeter-wave radar, to measure/determine the blood pressure. Some embodiments may be used for other purposes, such as for determining the skin elasticity of a human, for example. Some embodiments may be used in animals, such as dogs, cats, etc.

In an embodiment of the present invention, a blood pressure sensing device includes a millimeter-wave radar that is used, in cooperation with a temperature sensor, to determine a blood pressure of a human. The millimeter-wave radar is used to measure a distension of a portion of a skin covering a blood vessel of the human. A temperature sensor measures the temperature of the portion of the skin. The blood pressure of the human is determined based on the measured distension of the skin and the measured temperature. In some embodiments, the blood pressure sensing device is a watch or (e.g., fitness) band that is worn in a wrist of the human.

In some embodiments, the blood pressure sensing device is calibrated with respect to the temperature of the skin. During the calibration step, skin distension measurements, skin temperature measurements, and blood pressure measurements are taken while the portion of the skin is heated by the radiation produced by the millimeter-wave radar. The skin distension measurements, skin temperature measurements, and blood pressure measurements are used to generate a relationship between skin distension, skin temperature, and blood pressure (which may be stored in the form of a look-up table). During normal operation, the blood pressure sensing device determines the blood pressure of the human based on the measured skin distension, measured skin temperature, and the determined relationship (e.g., stored in the look-up table).

Advantages of some embodiments include the continuous determination (e.g., in real time) of the blood pressure of a human in a non-invasive, cuffless manner, and without applying pressure to the skin for purposes of blood pressure determination.

It is known that the arterial pressure P may be related to the Young's modulus E, e.g., by $$E = E_o e^{aP} \quad (1)$$

where $E_o$ is the Young's modulus for zero arterial pressure, and a is a parameter related to the blood vessel. The Young's modulus E may be understood as a mechanical property that quantifies the tensile stiffness of a solid material (such as the walls of the blood vessel), and may be given by $$E = \frac{\sigma}{\varepsilon} \quad (2)$$

where $\sigma$ represents the tensile stress (force per unit area) and $\varepsilon$ represents the axial strain (proportional deformation).

As shown, for example, by Equations 1 and 2, there is a relationship between axial strain $\varepsilon$, e.g., of the blood vessel wall, and arterial pressure P. The relationship between axial strain $\varepsilon$ and arterial pressure P may be given by $$P = \frac{\ln\left(\frac{\sigma}{\varepsilon E_o}\right)}{a}. \quad (3)$$

The model illustrated by Equations 1 to 3 is one of many possible models that may be used to determine blood pressure. Other models include the two-parallel spring model and the two-dimensional hyperelastic model, for example.

The arterial distension may be indicative of axial strain $\varepsilon$ and, thus, may be indicative of arterial pressure. Skin distension may be indicative of arterial distension and, thus, may be indicative of arterial pressure. For example, FIGS. 2A and 2B show diagrams 200 and 220 illustrating arterial distension and skin distension at the points of diastolic pressure and systolic pressure, respectively.

Figure 2A:
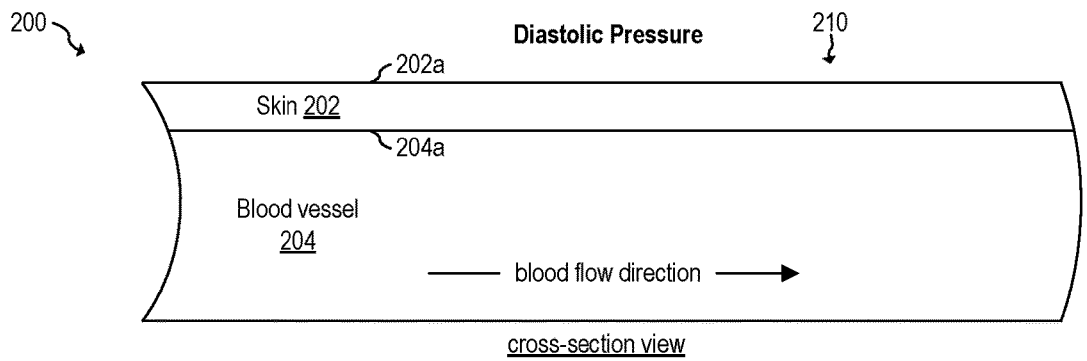
FIGS. 2A and 2B show diagrams and illustrating arterial distension and skin distension at the points of diastolic pressure and systolic pressure, respectively.
Figure 2B:
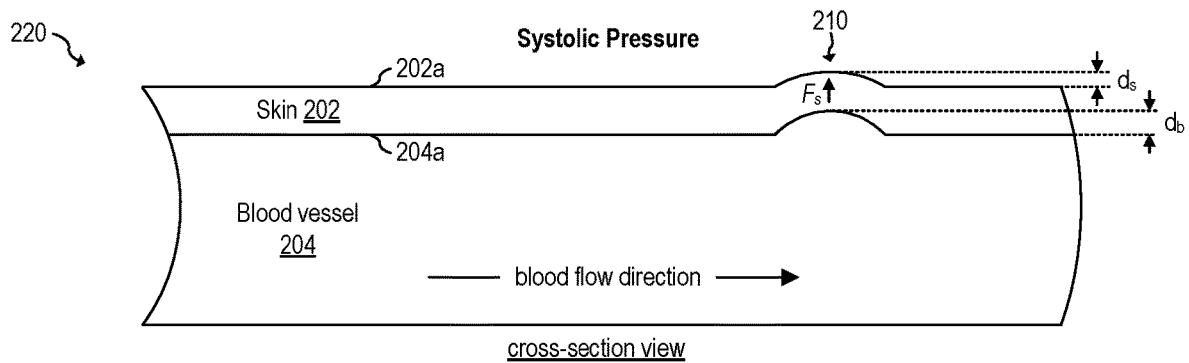

As shown in FIG. 2B, when location 210 experiences the pressure resulting from the maximum contraction of the heart, blood vessel 204 deforms at location 210 and exhibits distension with a magnitude $d_b$. The deformation of blood vessel 204 at location 210 exerts a force in skin 202, which in turn deforms at location 210 and exhibits distension with magnitude $d_s$. It is understood that there may be a time delay between the deformation of surface 204a of blood vessel 204 and the deformation of surface 202a of skin 202.

As shown in FIG. 2A, when location 210 experience the effects of diastolic pressure $P_{DBP}$, the blood vessel 204 and the skin 202 may not exhibit distension (e.g., $d_s=d_b=0$ mm).

Blood vessel 204 may be, e.g., the radial artery. Other blood vessels, such as other arteries, may also be used.

The amplitude of the arterial distension $d_b$ may track (although possibly with some distortion), the shape of blood pressure waveform (e.g., 100). Similarly, the amplitude of the skin distension $d_s$ may track (although possibly with some distortion), the shape of blood pressure waveform (e.g., 100). In some cases, the maximum (peak) skin distension may be 2.5 mm or lower. Peak skin distensions higher than 2.5 mm are also possible.

In some cases, the magnitude of skin distension $d_s$ and the magnitude of arterial distension $d_b$ may be different, even after accounting for any propagation delays. For example, the peak of skin distension $d_s$ and arterial distension $d_b$ for a particular pulse may be different.

A factor that affects the amount of skin distension $d_s$ based on the amount of arterial distension $d_b$ is skin elasticity. Skin elasticity may be understood as the ability of the skin to stretch while still remaining firm and shapely. For example, for a given arterial distension $d_b$, higher skin elasticity (higher ability to stretch) may result in higher skin distension $d_s$, while lower skin elasticity may results in lower skin distension $d_s$. For example, the magnitude of skin distension $d_s$ during a pulse may be modeled as a spring loaded system, given by $$F_s = K_s d_s \quad (4)$$

where $F_s$ represents the force that the wall of the blood vessel exerts on the skin at location 210, and $K_s$ represents the spring constant. Spring constant $K_s$ may be indicative of the skin elasticity.

Skin elasticity may be affected by factors such as, e.g., aging and temperature. Elasticity changes due to, e.g., aging, may be slow to take effect. For example, as a human ages, the skin may become less elastic. Changes in skin elasticity due to aging may take month or years to be noticeable. Changes in temperature of the skin, however, may affect skin elasticity in a faster manner. For example, the skin temperature may increase by more than 1° C. within 5 minutes of direct sun exposure, and may increase by higher amounts (e.g., 7° C. or more) under some conditions within 2 hours of direct sun exposure. Evaporative heat loss may also contribute to changes (e.g., decrease) in skin temperature.

In an embodiment of the present invention, blood pressure is estimated by measuring skin distension. Changes in skin elasticity resulting from changes in skin temperature are compensated for by applying a compensation coefficient selected based on the temperature of the skin.

Figure 3:
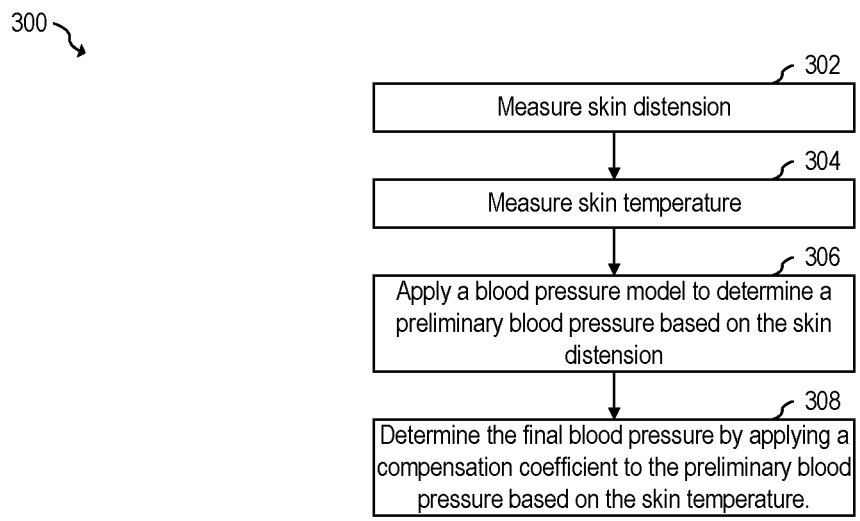
FIG. 3 shows a flow chart of an embodiment method to determine blood pressure based on skin distension, according to an embodiment of the present invention.

FIG. 3 shows a flow chart of embodiment method 300 to determine blood pressure based on skin distension, according to an embodiment of the present invention. Method 300 includes steps 302, 304, 306, and 308.

During step 302, the skin distension $d_s$ is measured, e.g., at location 210. In some embodiments, measuring the skin distension includes measuring or determining the peak skin distension $d_{s\_peak}$. In some embodiments, measure the skin distension includes generating a continuous distension signal. In some embodiments, the skin distension measurements may be stored in (e.g., volatile) memory.

In some embodiments, the skin distension may be measured using a capacitive sensor, such as a piezo-electric sensor in contact with the skin (e.g., at location 210). For example, in some embodiments, the deformation of a piezo-electric sensor in contact with the skin produces a signal indicative of acceleration (e.g., of the skin at location 210). By integrating such signal twice, a displacement (distension) signal can be obtained.

As will be described in more details later, in some embodiments, a millimeter-wave radar may be used to measure the skin distension.

During step 304, the skin temperature is measured, e.g., at the same location 210. For example, in some embodiments, an infra-red (IR) sensor may be used to measure the skin temperature at location 210. In some embodiments, a thermistor in contact with the skin is used to measure the skin temperature at location 210. In some embodiments, the skin temperature measurements may be stored in (e.g., volatile) memory.

During step 306, a blood pressure model is applied to determine a preliminary blood pressure. For example, in some embodiments, the blood pressure model may be determined by making a plurality of controlled measurements in a human (or group of humans) to generate the relationship. For example, in some embodiments, a blood pressure model calibration step is performed in which the blood pressure of the human is monitored with a conventional blood pressure monitoring device, such as a CNAP simultaneously with measuring the skin distension $d_s$. A relationship may be generated in which the blood pressure (e.g., peak) generated by the CNAP can be predicted by the distension measured. In some embodiments, the prediction involves predicting the systolic pressure $P_{SBP\_PRE}$. For example, in some embodiments, the systolic pressure $P_{SBP\_PRE}$ is determined by $$P_{SBP\_PRE} = G_{SBP\_PRE} \cdot d_{s\_peak} \quad (5)$$

where $G_{SBP\_PRE}$ is a scalar determined based on the correlation between a plurality of skin distension measurements and their corresponding systolic blood pressure measurements from the conventional sensor (e.g., CNAP).

In some embodiments, since the shape of the distension signal may track the blood pressure waveform, in some embodiments, predicting the blood pressure includes applying a gain function to the distension signal to produce the blood pressure waveform. For example, in some embodiments, the relationship between the preliminary blood pressure signal $P_{PRE}(t)$ and the time domain skin distension signal $d_s(t)$ may be given by $$P_{PRE}(t) G_{PRE} \cdot d_s(t) \quad (6)$$

where $G_{PRE}$ is a scalar determined based on the measurements performed during the blood pressure model calibration step. In some embodiments, the gain used in Equation 6 may be frequency dependent.

In some embodiments, the relationship between skin distension $d_s$ and preliminary blood pressure may depend in one or more variable. In some embodiments, the relationship between skin distension $d_s$ and preliminary blood pressure may be non-linear.

In some embodiments, the relationship between p skin distension $d_s$ and preliminary blood pressure is generated for a group of humans that share similar characteristics (e.g., same age, gender, etc.), and the resulting relationship is applied to other humans sharing similar characteristics, thus, advantageously avoiding the generation of the relationship for each human.

During step 308, the blood pressure determined during step 306 (e.g., either the blood pressure signal $P_{PRE}(t)$ or the systolic pressure $P_{SBP\_PRE}$) is compensated for the skin temperature measured during step 304. For example, in some embodiments, a relationship between the preliminary blood pressure, actual blood pressure, and skin temperature may be generated by making a plurality of controlled measurements in a human (or group of humans). For example, in some embodiments, after performing the blood pressure model calibration step, preliminary blood pressure measurements are generated based on skin distension $d_s$ (e.g., at location 210) using the blood pressure model simultaneously with measuring the skin temperature (e.g., at location 210), and measuring blood pressure with a conventional blood pressure monitoring device, such as a CNAP. A relationship may be generated in which the blood pressure (e.g., peak) generated by the CNAP can be predicted by the preliminary blood pressure measurement and the temperature. For example, in some embodiments, the systolic pressure $P_{SBP}$ is determined by $$P_{SBP}(T) = G_{SBP\_TEMP}(T) \cdot P_{PRE} \quad (7)$$

where $G_{SBP\_TEMP}$ is a scalar determined based on the correlation between a plurality of preliminary systolic pressure measurements $P_{SBP\_PRE}$, the associated skin temperature measurement, and their corresponding systolic blood pressure measurements from the conventional sensor (e.g., CNAP).

In some embodiments, the relationship between the blood pressure signal $P(t)$ and the time domain preliminary blood pressure signal $P_{PRE}(t)$ may be given by $$P(t,T) = G_{PRE\_TEMP}(T) \cdot P_{PRE}(t) \quad (8)$$

where T represents the skin temperature associated with the preliminary blood pressure signal $P_{PRE}(t)$. In some embodiments, the gain used in Equation 8 may be frequency dependent.

In some embodiments, the relationship between preliminary blood pressure and blood pressure may be non-linear with respect to temperature.

In some embodiments, the relationship between preliminary blood pressure and blood pressure based on skin temperature is generated for a group of humans that share similar characteristics (e.g., same age, gender, etc.), and the resulting relationship is applied to other humans sharing similar characteristics, thus, advantageously avoiding the generation of the relationship for each human.

In some embodiments, the relationship between the preliminary blood pressure, actual blood pressure, and skin temperature may be stored in the form of LUT. For example, in some embodiments a LUT may include values of gain $G_{SBP\_TEMP}$ based on the skin temperature T. In some embodiments a LUT may include values of gain $G_{PRE}$ based on the skin temperature T.

In some embodiments, steps 302 and 304 may be performed simultaneously. In some embodiments, step 304 may be performed after (or during) step 306. In some embodiments, steps 306 and 308 may be performed simultaneously (e.g., by applying a single equation). For example, in some embodiments, blood pressure may be determined by $$P_{SBP}(T) = G_{SBP\_TEMP}(T) \cdot G_{SBP\_PRE} \cdot d_{s\_peak} = G_{SBP\_COMB}(T) \cdot d_{s\_peak} \quad (9)$$

or by $$P(t,T) = G_{PRE\_TEMP}(T) \cdot G_{PRE} \cdot D_s(t) = G_{comb}(T) \cdot D_s(t) \quad (10).$$

Equations 5-10 may also be implemented in the digital domain, e.g., substituting time t with discrete time n.

Figure 4A:
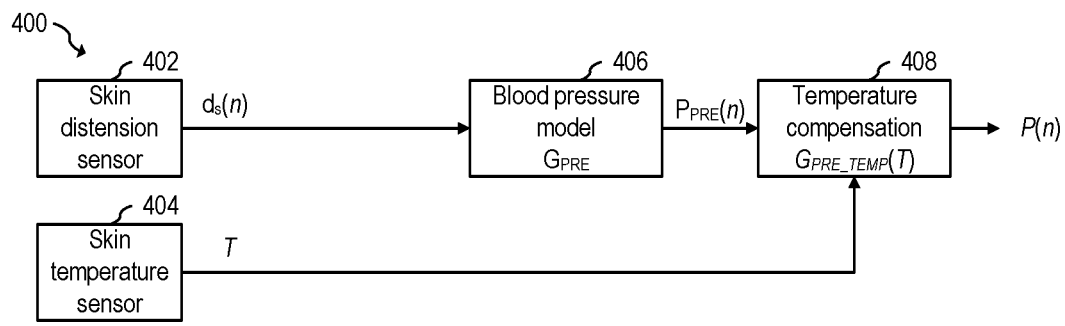
FIGS. 4A-4D show block diagrams illustrating the determination of blood pressure based on skin distension and skin temperature, according to embodiments of the present invention.

FIG. 4A shows block diagrams 400 illustrating the determination of blood pressure based on skin distension and skin temperature, according to embodiments of the present invention. Block diagram 400 shows a possible implementation of method 300. For example, as shown in FIG. 4A, skin distension sensor 402 generates skin distension signal $d_s(n)$ by measuring the deformation of the skin, e.g., at location 210 (e.g., step 302). Skin temperature sensor 402

(also referred to as a thermal sensor) generates skin temperature value T by measuring the skin temperature, e.g., at location 210 (e.g., step 304). Blood pressure model 406 is used to generate preliminary blood pressure signal $P_{PRE}(n)$ based on the skin distension signal $d_s(n)$ (e.g., step 306, e.g., using Equation 6). Temperature compensation model 408 generates blood pressure signal P(n) based on preliminary blood pressure signal $P_{PRE}(n)$ and the skin temperature T (e.g., step 308, e.g., using Equation 8).

In some embodiments, skin distension sensor 402 may be implemented using a millimeter-wave radar.

In some embodiments, skin temperature sensor 404 may be implemented with an IR sensor. In some embodiments, skin temperature sensor 404 may be implemented with a thermistor in contact with the surface of the skin.

In some embodiments, blood pressure model 406 and temperature compensation model 408 may be implemented in a general purpose or custom controller (e.g., microcontroller) or processor.

Figure 4B:
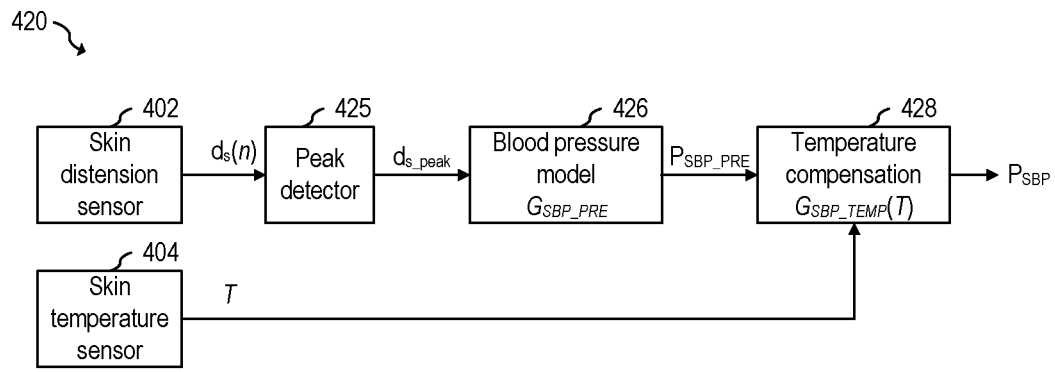

FIG. 4B shows block diagrams 420 illustrating the determination of blood pressure based on skin distension and skin temperature, according to embodiments of the present invention. Block diagram 420 shows a possible implementation of method 300. For example, as shown in FIG. 4B, skin distension sensor 402 generates skin distension signal $d_s(n)$ (e.g., step 302). Peak detector generates peak skin distension values $d_{s\_peak}$ from a distension signal $d_s(n)$ (e.g., step 302). Skin temperature sensor 402 generates skin temperature value T (e.g., step 304). Blood pressure model 426 is used to generate preliminary systolic blood pressure value $P_{SBP\_PRE}$ based on the peak skin distension values $d_{s\_peak}$ (e.g., step 306, e.g., using Equation 5). Temperature compensation model 428 generates systolic blood pressure $P_{SBP}$ based on preliminary blood pressure value $P_{PRE}(n)$ and the skin temperature T (e.g., step 308, e.g., using Equation 7).

Peak detector 425 is configured to detect the peak of signal $d_s(n)$ and may be implemented, e.g., digitally, in any way known in the art.

In some embodiments, blood pressure model 426 and temperature compensation model 428 may be implemented in a general purpose or custom controller (e.g., microcontroller) or processor.

Figure 4C:
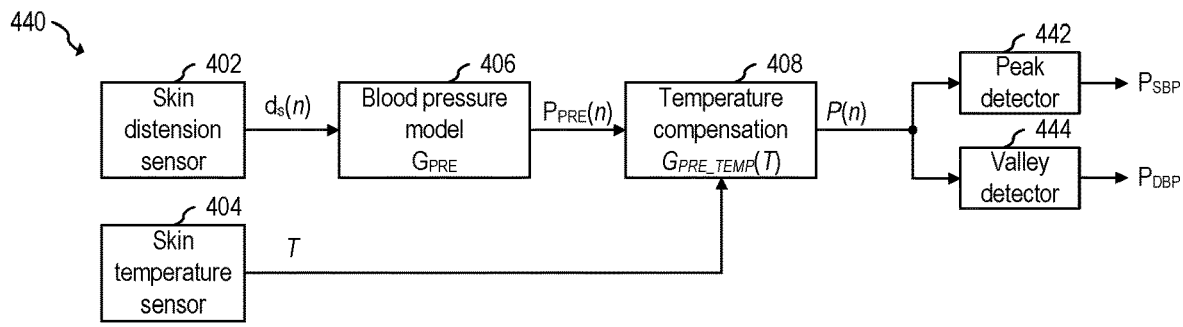

FIG. 4C shows block diagrams 440 illustrating the determination of blood pressure based on skin distension and skin temperature, according to embodiments of the present invention. As illustrated in FIG. 4C, systolic and diastolic blood pressure values ($P_{SBP}$ and $P_{DBP}$) may be obtained from the blood pressure signal generates by the temperature compensation model 408.

Peak detector 442 is configured to detect the peak of signal P(n) and may be implemented, e.g., digitally, in any way known in the art. Valley detector 444 is configured to detect the valley of signal P(n) and may be implemented, e.g., digitally, in any way known in the art.

Figure 4D:
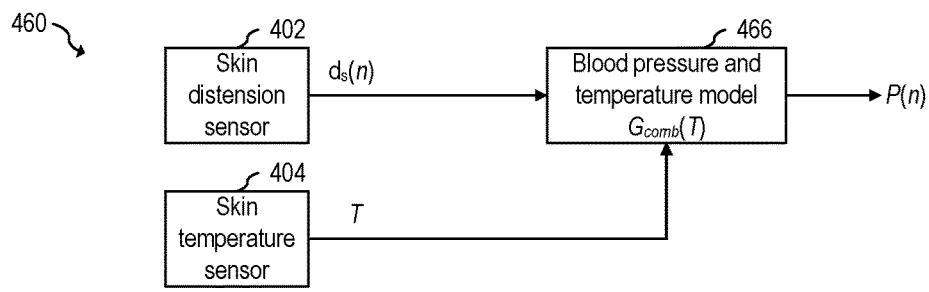

FIG. 4D shows block diagrams 460 illustrating the determination of blood pressure based on skin distension and skin temperature, according to embodiments of the present invention. Block diagram 460 shows a possible implementation of method 300. For example, as shown in FIG. 4D, skin distension sensor 402 generates skin distension signal $d_s(n)$ (e.g., step 302). Skin temperature sensor 402 generates skin temperature value T (e.g., step 304). Blood pressure and temperature model 466 is used to generate blood pressure signal P(t) based on skin distension signal $d_s(n)$ and the skin temperature T (e.g., steps 306 and 308, e.g., using Equation 10).

In some embodiments, blood pressure and temperature model 466 may be implemented in a general purpose or custom controller (e.g., microcontroller) or processor.

Figure 5:
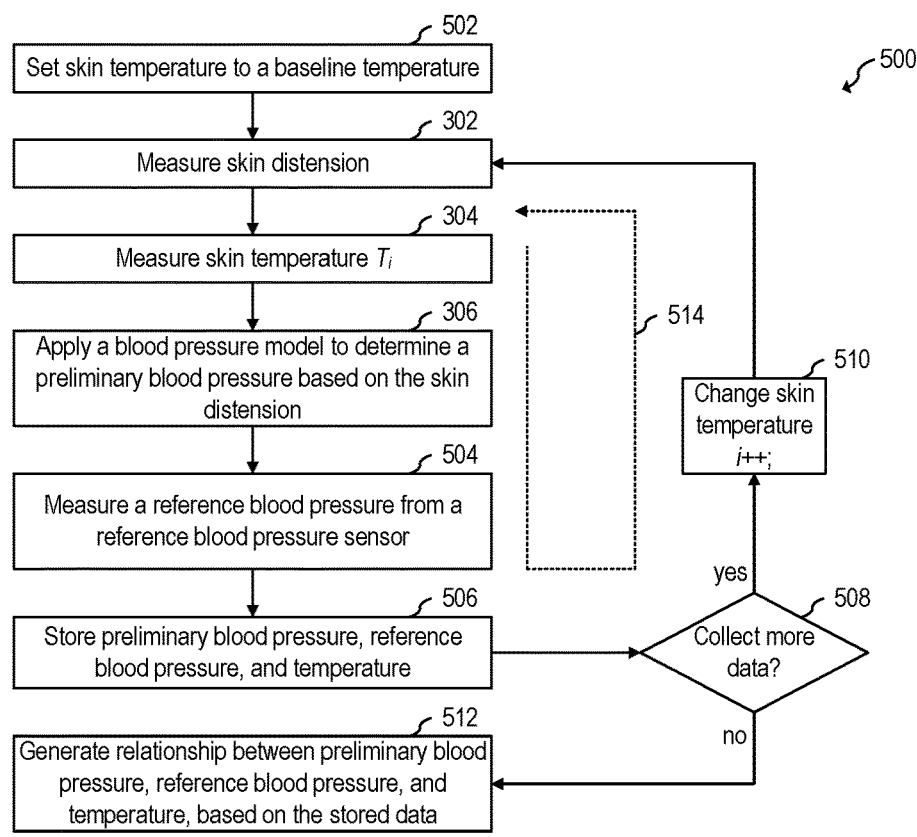
FIG. 5 shows a flow chart of an embodiment method of temperature calibration for compensating a preliminary blood pressure measurement based on skin temperature, according to an embodiment of the present invention.

FIG. 5 shows a flow chart of embodiment method 500 of temperature calibration for compensating a preliminary blood pressure measurement (e.g., generated during step 306) based on a skin temperature (e.g., measured during step 304), according to an embodiment of the present invention. Method 500 includes steps 502, 302, 304, 306, 504, 506, 508, 510 and 512. Steps 302, 304, and 306 may be performed in a similar manner as in method 300.

In some embodiments, method 500 may be performed on a given human such that, e.g., method 300 performs temperature compensation (e.g., step 308) for such given human. In some embodiments, method 500 may be performed on a group of humans sharing one or more characteristics (e.g., age, gender, etc.) such that, e.g., method 300 performs temperature compensation (e.g., step 308) for other humans, e.g., sharing the same one or more characteristics. Thus, in some embodiments, step 308 may be used to correct variations or errors in blood pressure measurements that would manifest from different skin elasticity across a population.

During step 502, the skin temperature (e.g., at location 210) is set, or is verified to be, at a baseline temperature. For example, in some embodiments, the baseline temperature represents the initial temperature of the skin (e.g., at location 210). In some embodiments, the temperature set during step 502 is the same temperature used for the generation of the blood pressure model (e.g., 406, 426).

During steps 302, 304, and 306, the skin distension is measured (e.g., at location 210), the skin temperature (e.g., at location 210), and the preliminary blood pressure is generated, respectively.

During step 504, a reference blood pressure is measured, e.g., simultaneously with the measurement of the skin distension measured during step 302 (e.g., so that the distension measurement and the reference blood pressure measurement relate to the same pulse). In some embodiments, the reference blood pressure measurement is performed using a CNAP device. Other reference blood pressure measurement devices/methods, such as relying on an auscultatory method, PTT, or other, may also be used.

During step 506, the relationship between the preliminary blood pressure measurement and the reference blood pressure measurement is stored, e.g., in a LUT. For example, during step 506, the gain function $G_{PRE\_TEMP}$ at temperature $T_i$ (measured during step 304) is generated such that the pulse waveforms generated during steps 306 ($P_{PRE\_i}$) and 504 ($P_{ref\_i}$), e.g., approximately, match, such as shown in Equation 11.

$$P_{ref\_i}(t,T_i) = G_{PRE\_TEMP}(T_i) \cdot P_{PRE\_i}(t) \quad (11)$$

In some embodiments, during step 506, the gain function $G_{SBP\_TEMP}$ at temperature $T_i$ (measured during step 304) is generated such that the reference systolic blood pressure $P_{SBPREF\_i}$ measured during step 504 and the preliminary blood pressure measurement $P_{PRE\_i}$ measured during step 306 (e.g., approximately) match, such as shown in Equation 12.

$$P_{SBPREF\_i}(T_i) = G_{SBP\_TEMP}(T_i) \cdot P_{PRE\_i} \quad (12)$$

As shown in FIG. 5, steps 302, 304, 306, 504, 506 and 510 may be performed in a loop (514). The time duration of loop 514 may be referred to as a calibration time interval. The determination of when to stop the loop 514 is performed during step 508. For example, in some embodiments, a timer is used such that data is collected for a predetermined period of time (e.g., 5 minutes). The predetermined period may be shorted than 5 minutes (e.g., 4 minutes, or less), or longer than 5 minutes (e.g., 10 minutes, or more).

In some embodiments, data is collected for a predetermined temperature range (e.g., between 15° C. and 35° C.). For example, in some embodiments, data is collected for a predetermined range $T_{range}$ (e.g., 20° C.), where, e.g., the lowest temperature is the baseline temperature $T_{base}$ and the highest temperature is $T_{base}+T_{range}$.

In some embodiments, a predetermined number of data samples are collected. For example, in some embodiments, loop 514 is iterated 100 times. More than 100 iterations, such as 120, 200, or more, or less than 100 iterations, such as 80, 50, or less, are also possible.

Figure 11A:
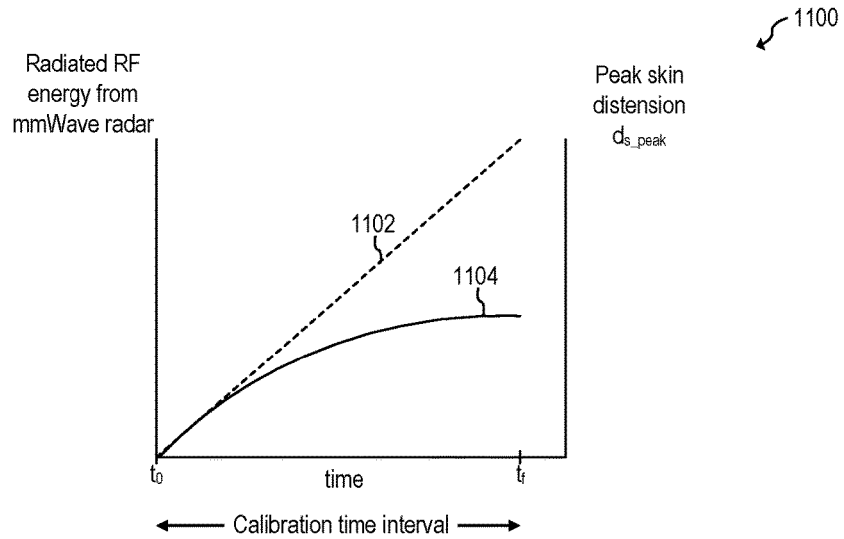
FIG. 11A shows a plot illustrating the progression over time of radiated RF energy from the millimeter-wave radar system of FIG. 8 and the peak skin distension generated by the millimeter-wave radar system of FIG. 8, according to an embodiment of the present invention.
Figure 11B:
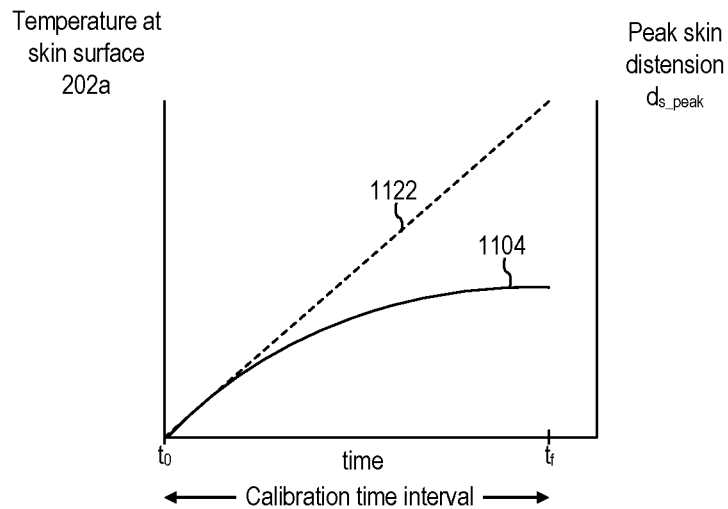
FIG. 11B show a plot illustrating the progression over time of the temperature of a skin surface and the associated peak skin distension, according to an embodiment of the present invention.

In some embodiments, as the skin temperature increases, the skin elasticity increase decreases (e.g., as can be seen in FIG. 11B by the progression over time of the rate of change of the peak skin distension $d_{s\_peak}$, as shown by curve 1104, which is indicative of skin elasticity, and the skin temperature, as shown by curve 1122). Thus, in some embodiments, data is collected while the rate of change of the gain function (e.g., $G_{PRE\_TEMP}(T)$, $G_{SBP\_TEMP}(T)$), with respect to temperature, is larger than a predetermined threshold.

During step 510, the temperature of the skin (e.g., at location 210) is changed. For example, in some embodiments, radiation from a millimeter-wave radar may be used to heat the skin (e.g., at location 210). Other methods for changing the temperature of the skin may also be used. For example, in some embodiments, other heat generation devices, such as a resistance in contact or near the skin (e.g., at location 210) may be used. In some embodiments, ice or spayed water may be applied (e.g., to location 210) during step 510.

In some embodiments, energy is applied to the skin surface 202a at location 210 or removed from the skin surface 202a at location 210 linearly. In some embodiments, energy is applied to the skin surface 202a at location 210 or removed from the skin surface 202a at location 210 non-linearly (e.g., exponentially).

During step 512, the relationship between the preliminary blood pressure and the reference (e.g., final) blood pressure, based on skin temperature, is generated. For example, in some embodiments, generating the relationship includes making the LUT (e.g., generated during steps 506) accessible during performance of, e.g., method 300 (such that the LUT acts as the gain function, e.g., during step 308, such as in Equations 7 or 8). In some embodiments, generating the relationship includes generating an equation that approximates the relationship generated during steps 506 (e.g., a best fit function that tracks the relationship generated during steps 506) and making such generated function accessible during performance of, e.g., method 300 (such that the generated function is used as the gain function, e.g., during step 308, such as in Equations 7 or 8).

Figures 6, 7:
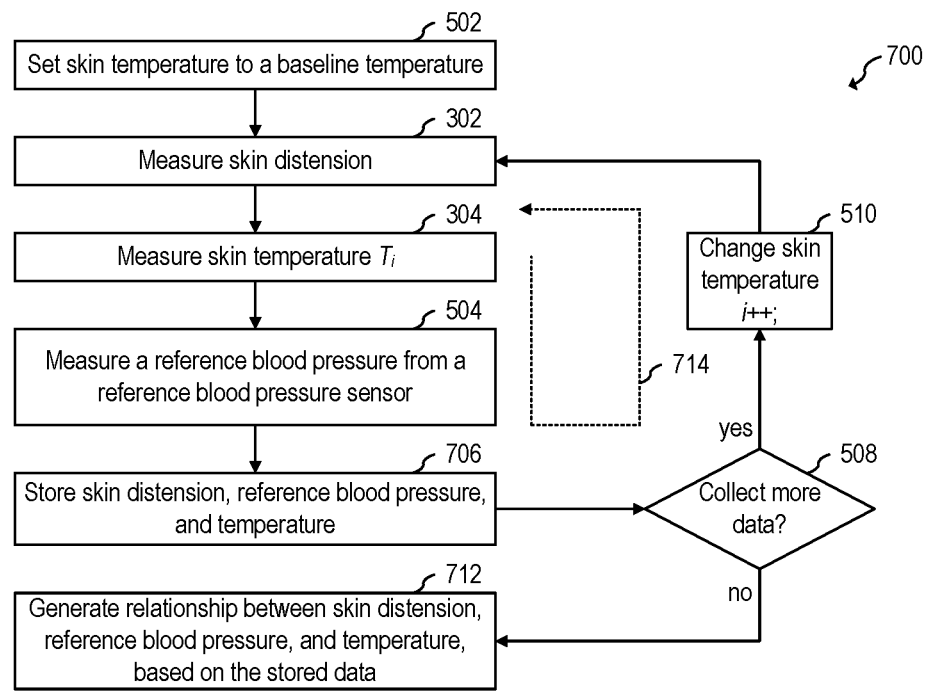
FIG. 6 shows a look-up table (LUT) for storing a relationship of a final blood pressure based on skin temperature, according to an embodiment of the present invention.
FIG. 7 shows a flow chart of an embodiment method of blood pressure and temperature calibration for relating a skin distension measurement to a blood pressure measurement based on skin temperature, according to an embodiment of the present invention.

In some embodiments, the values of the gain functions (e.g., $G_{PRE\_TEMP}(T)$, $G_{SBP\_TEMP}(T)$) for each temperature $T_i$ (collected during loop 514) are stored in a LUT. For example, FIG. 6 shows LUT 600 for storing a relationship, e.g., between a preliminary blood pressure (e.g., generated during step 306) and a final blood pressure (e.g., generated during step 308) based on skin temperature (e.g., measured during step 304), according to an embodiment of the present invention. In some embodiments, LUT 600 is stored in (e.g., non-volatile) memory.

As shown in FIG. 6, LUT 600 may include N rows, which may be, e.g., sequentially populated during each iteration of loop 514. In some embodiments, the first row of LUT 600 may correspond to the baseline temperature ($T_1=T_{base}$).

In some embodiments, N may be larger than 50, such as 100, 120, 200, or more. In some embodiments, N may be smaller than 50, such as 48, 30, or less.

In some embodiments, gain function G(T) may correspond to $G_{SBP\_TEMP}(T)$ (e.g., of Equation 7). In some embodiments, gain function G(T) may correspond to $G_{PRE\_TEMP}(T)$ (e.g., of Equation 8). Gain functions $G_1$ to $G_N$ may be referred to as compensation coefficients $G_1$ to $G_N$.

In some embodiments, LUT 600 may be used during step 308 (e.g., when performing method 300) for determining the final blood pressure. For example, in some embodiments, the temperature (e.g., $T_i$) measured during step 304 may be used to select the gain function $G_i$ in the corresponding row in LUT 600, and then used the selected gain function $G_i$ to determine the final blood pressure (e.g., using Equations 7 or 8). LUT 600 may be used, for example, by temperature compensation model 408, and 428. As will be described in more detail later, LUT 600 may also be used by blood pressure and temperature model 466.

In some embodiments, the temperature calibration may be performed simultaneously with the blood pressure model calibration. For example, FIG. 7 shows a flow chart of embodiment method 700 of blood pressure and temperature calibration for relating a skin distension measurement (e.g., measured during step 302) to a blood pressure measurement based on skin temperature (e.g., measured during step 304), according to an embodiment of the present invention. Method 700 includes steps 502, 302, 304, 504, 706, 508, 510 and 712. Steps 502, 302, 304, 504, 508, and 510 may be performed in a similar manner as in method 500.

In some embodiments, method 700 may be performed on a given human such that, e.g., method 300 generates the final blood pressure measurement (e.g., steps 306 and 308 combined) for such given human. In some embodiments, method 700 may be performed on a group of humans sharing one or more characteristics (e.g., age, gender, etc.) such that, e.g., method 300 generates the final blood pressure measurement (e.g., steps 306 and 308 combined) for other humans, e.g., sharing the same one or more characteristics.

As can be seen in FIGS. 5 and 7, method 700 is similar to method 500. Method 700, however, stores a relationship between skin distension, and a reference blood pressure (e.g., in a LUT) during step 706 instead of performing step 506. After loop 714 finish iterating (after the calibration time interval), the relationship between the skin distension and the reference (e.g., final) blood pressure, based on skin temperature, is generated during step 712. For example, in some embodiments, generating the relationship includes making the LUT (e.g., generated during steps 706) accessible during performance of, e.g., method 300 (such that the LUT acts as the gain function, e.g., during the combined steps of 306 and 308, such as in Equations 9 or 10). In some embodiments, generating the relationship includes generating an equation that approximates the relationship generated during steps 706 (e.g., a best fit function that tracks the relationship generated during steps 706) and making such generated function accessible during performance of, e.g., method 300 (such that the LUT acts as the gain function, e.g., during the combined steps of 306 and 308, such as in Equations 9 or 10).

In some embodiments, gain function G(T) of LUT 600 may correspond to $G_{SBP\_comb}(T)$ (e.g., of Equation 9). In some embodiments, gain function G(T) may correspond to $G_{comb}(T)$ (e.g., of Equation 1).

In some embodiments, the spring constant $K_s$ of Equation 4 may be determined, e.g., during methods 500 or 700, for each skin temperature $T_i$, (e.g., assuming force $F_s$ is constant during loops 514 and 714) and each spring constant ($K_{s1}$ to $K_{sN}$) may be stored in LUT 600 in the respective rows (1 to N).

In some embodiments, the spring constant $K_s$ of Equation 4 (e.g., stored in LUT 600) may be correlated with actual skin elasticity (e.g., as determined by a cutometer).

Figure 8:
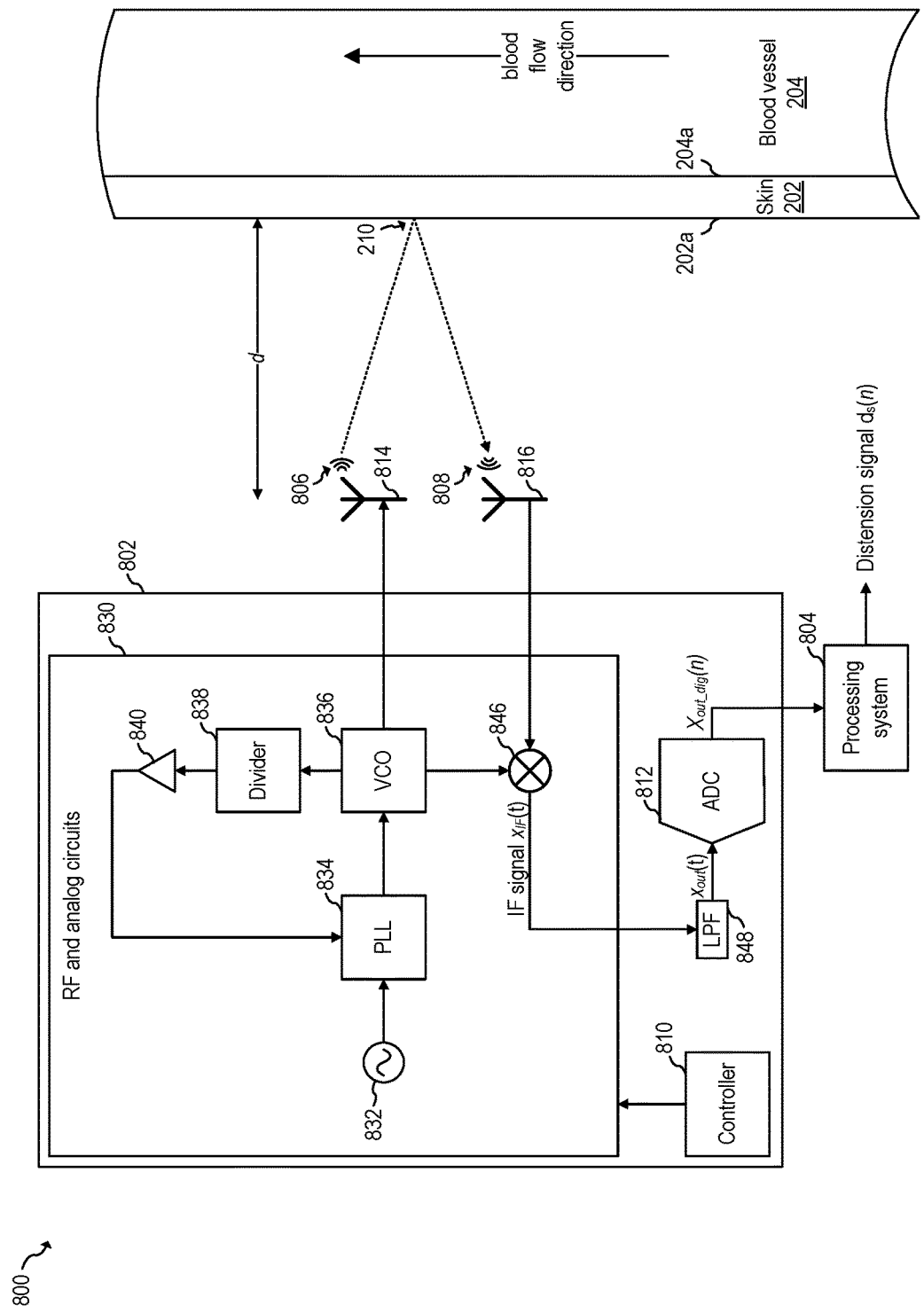
FIG. 8 shows a schematic diagram of a millimeter-wave radar system, according to an embodiment of the present invention.

FIG. 8 shows a schematic diagram of millimeter-wave radar system 800, according to an embodiment of the present invention. Millimeter-wave radar system 800 may be used to generate distension signal $d_s(n)$, e.g., during step 302. Skin distension sensor 402 may be implemented as millimeter-wave radar system 800. Millimeter-wave radar system 800 includes millimeter-wave radar sensor 802 and processing system 804.

During normal operation, millimeter-wave radar sensor 802 operates as a frequency-modulated continuous-wave (FMCW) radar sensor and transmits a plurality of TX radar signals 806, such as chirps, towards skin 202 using transmitter (TX) antenna 114. The radar signals 806 are generated using RF and analog circuits 830. The radar signals 806 may be in the 20 GHz to 122 GHz range, such as between 57 GHz and 63 GHz, or between 118 GHz and 122 GHz, for example.

Millimeter-wave radar sensor has a field-of-view (FoV) aimed towards skin 202 at location 210. In some embodiments, the distance d between transmitting antenna 114 and skin surface 202a may be fixed. In some embodiments, distance d may be, e.g., 10 mm. Other distances d, such as 15 mm, 20 mm, or higher, or lower than 10 mm, such as in contact with the skin surface 202a, may also be used.

The radar signals 806 are reflected by skin surface 202a. The reflected radar signals 808, which are also referred to as the echo signal, are received by receiver (RX) antennas 816. RF and analog circuits 830 processes the received reflected radar signals 808 using, e.g., band-pass filters (BPFs), low-pass filters (LPFs), mixers, low-noise amplifier (LNA), and/or intermediate frequency (IF) amplifiers in ways known in the art to generate an analog signal $x_{out}(t)$.

The analog signal $x_{out}(t)$ is converted to raw digital data $x_{out\_dig}(n)$ using ADC 812. The raw digital data $x_{out\_dig}(n)$ is processed by processing system 804 to generate distension signal $d_s(n)$.

In some embodiments, radar system 800 may include a plurality of transmitting antennas 114 and/or a plurality of receiving antennas 116.

Controller 810 controls one or more circuits of millimeter-wave radar sensor 802, such as RF and analog circuit 830 and/or ADC 812. Controller 810 may be implemented, e.g., as a custom digital or mixed signal circuit, for example. Controller 810 may also be implemented in other ways, such as using a general purpose processor or controller, for example. In some embodiments, processing system 804 implements a portion or all of controller 810.

Processing system 804 may be implemented with a general purpose processor, controller or digital signal processor (DSP) that includes, for example, combinatorial circuits coupled to a memory. In some embodiments, processing system 804 may be implemented as an application specific integrated circuit (ASIC). In some embodiments, processing system 804 may be implemented with an ARM, RISC, or x86 architecture, for example. In some embodiments, processing system 804 may include an artificial intelligence (AI) accelerator. Some embodiments may use a combination of hardware accelerator and software running on a DSP or general purpose microcontroller. Other implementations are also possible.

In some embodiments, processing system 804 may implement method 300, 500, and/or 700, may implement LUT 600, and/or may implement blocks 406, 408, 425, 426, 428, 442, 444, and/or 466.

In some embodiments, millimeter-wave radar sensor 802 and a portion or all of processing system 804 may be implemented inside the same integrated circuit (IC). For example, in some embodiments, millimeter-wave radar sensor 802 and a portion or all of processing system 804 may be implemented in respective semiconductor substrates that are integrated in the same package. In other embodiments, millimeter-wave radar sensor 802 and a portion or all of processing system 804 may be implemented in the same monolithic semiconductor substrate. Other implementations are also possible.

Some embodiments may be implemented with a partial distributed implementation in which a portion of processing system 804 is implemented remotely, such as in the cloud, and may communicate with the local portion of processing system 804 (e.g., implemented near or inside millimeter-wave radar sensor 802) via the Internet. For example, in some embodiments, a remote server (e.g., in the cloud) may store LUT 600 and may be configured to perform post processing and/or assist in real time processing when performing one or more steps of methods 300, 500, and/or 700. For example, in some embodiments, steps 306 and 308 may be performed in a remote server and the results (e.g., the determined blood pressure) sent back to the local portion of processing system 804 via the Internet. Other implementations are also possible.

As a non-limiting example, RF and analog circuits 830 may be implemented, e.g., as shown in FIG. 8. During normal operation, VCO 836 generates a radar signal, such as a linear frequency chirp (e.g., from 57 GHz to 64 GHz, or from 76 GHz to 77 GHz, or from 118 GHz to 122 GHz), which is transmitted by transmitting antenna 814. The VCO 836 is controlled by PLL 834, which receives a reference clock signal (e.g., 80 MHz) from reference oscillator 832. PLL 834 is controlled by a loop that includes frequency divider 838 and amplifier 840.

The TX radar signal 806 transmitted by transmitting antenna 814 is reflected by skin surface 202a and is received by receiving antenna 116. The echo received by receiving antenna 116 is mixed with a replica of the signal transmitted by transmitting antenna 814 using mixer 846 to produce intermediate frequency (IF) signal $x_{IF}(t)$ (also known as beat signals). In some embodiments, the beat signals $x_{IF}(t)$ has a bandwidth between 10 kHz and 1 MHz. Beat signals with a bandwidth lower than 10 kHz or higher than 1 MHz is also possible.

Beat signal $x_{IF}(t)$ is filtered with low-pass filters (LPF) 848 and then sampled by ADC 812. ADC 812 is advantageously capable of sampling the filtered beat signal $x_{out}(t)$ with a sampling frequency that is much smaller than the frequency of the signal received by receiving antenna 116. Using FMCW radars, therefore, advantageously allows for a compact and low cost implementation of ADC 812, in some embodiments.

The raw digital data $x_{out\_dig}(n)$, which in some embodiments include the digitized version of the filtered beat signal $x_{out}(t)$ is (e.g., temporarily) stored, e.g., in matrices of $N_c \times N_s$ per receiver antenna 816, where $N_c$ is the number of chirps considered in a frame and $N_s$ is the number of transmit samples per chirp, for further processing by processing system 804.

In some embodiments, ADC 812 is a 12-bit ADC with multiple inputs. ADCs with higher resolution, such as 14-bits or higher, or with lower resolution, such as 10-bits, or lower, may also be used. In some embodiments, an ADC per receiver antenna may be used. Other implementations are also possible.

Figure 9:
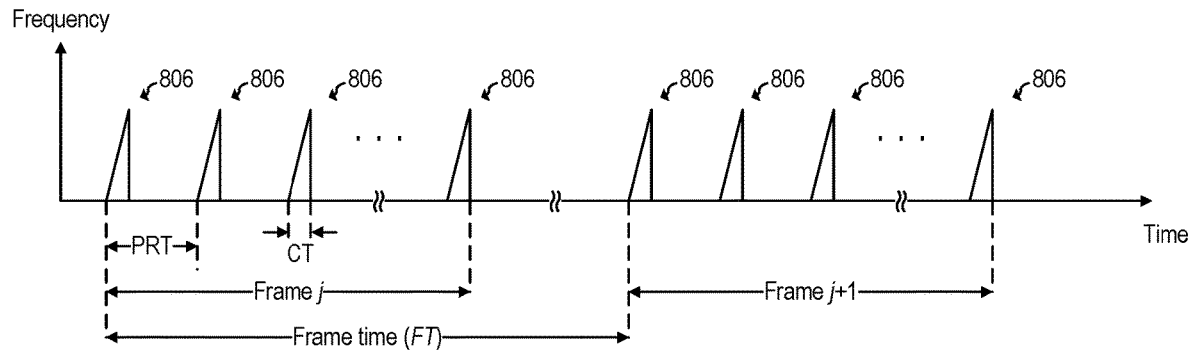
FIG. 9 shows a sequence of chirps transmitted by the transmitter antenna of FIG. 8, according to an embodiment of the present invention.

FIG. 9 shows a sequence of chirps 806 transmitted by TX antenna 814, according to an embodiment of the present invention. As shown by FIG. 9, chirps 806 are organized in a plurality of frames and may be implemented as up-chirps. Some embodiments may use down-chirps or a combination of up-chirps and down-chirps, such as up-down chirps and down-up chirps. Other waveform shapes may also be used.

As shown in FIG. 9, each frame may include a plurality of chirps 806 (also referred to, generally, as pulses). For example, in some embodiments, the number of pulses in a frame is 16. Some embodiments may include more than 16 pulses per frame, such as 20 pulses, 32 pulses, or more, or less than 16 pulses per frame, such as 10 pulses, 8 pulses, 4 or less. In some embodiments, each frame includes only a single pulse.

Frames are repeated every FT time. In some embodiments, FT time is 50 ms. A different FT time may also be used, such as more than 50 ms, such as 60 ms, 100 ms, 200 ms, or more, or less than 50 ms, such as 45 ms, 40 ms, or less.

In some embodiments, the FT time is selected such that the time between the beginning of the last chirp of frame j and the beginning of the first chirp of frame j+1 is equal to PRT. Other embodiments may use or result in a different timing.

The time between chirps of a frame is generally referred to as pulse repetition time (PRT). In some embodiments, the PRT is 5 ms. A different PRT may also be used, such as less than 5 ms, such as 4 ms, 2 ms, or less, or more than 5 ms, such as 6 ms, or more.

The duration of the chirp (from start to finish) is generally referred to as chirp time (CT). In some embodiments, the chirp time may be, e.g., 64 µs. Higher chirp times, such as 128 µs, or higher, may also be used. Lower chirp times, may also be used.

In some embodiments, the chirp bandwidth may be, e.g., 4 GHz. Higher bandwidth, such as 6 GHz or higher, or lower bandwidth, such as 2 GHz, 1 GHz, or lower, may also be possible.

In some embodiments, the sampling frequency of millimeter-wave radar sensor 802 may be, e.g., 1 MHz. Higher sampling frequencies, such as 2 MHz or higher, or lower sampling frequencies, such as 500 kHz or lower, may also be possible.

In some embodiments, the number of samples used to generate a chirp may be, e.g., 64 samples. A higher number of samples, such as 128 samples, or higher, or a lower number of samples, such as 32 samples or lower, may also be used.

Figure 10:
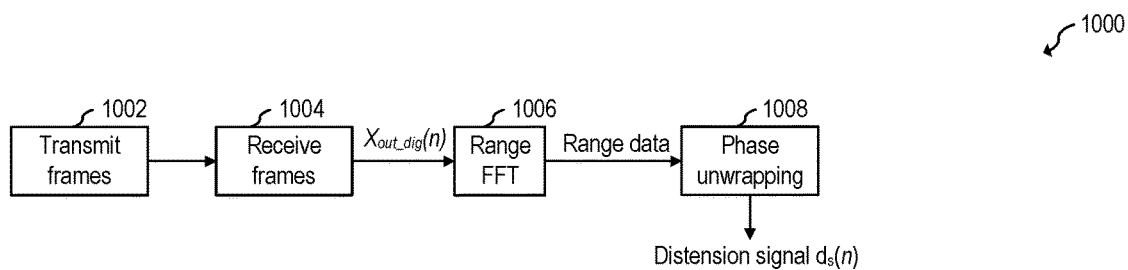
FIG. 10 shows a flow chart of an embodiment method for generating a skin distension signal from reflected radar signals, according to an embodiment of the present invention.

FIG. 10 shows a flow chart of embodiment method 1000 for generating a skin distension signal from reflected radar signals, according to an embodiment of the present invention. Method 1000 may be performed, e.g., by processor 804.

During step 1002, millimeter-wave radar 802, transmits, e.g., linear chirps 806 organized in frames using transmitting antenna 814. After reflection from skin surface 202a, receiving antenna 816 receives reflected chirps during step 1004, and raw digital data $x_{out\_dig}(n)$ is generated based on such reflected chirps. For example, in some embodiments, during step 1004, the transmitted and received radar signals are mixed to generate an IF signal. The IF signal is then filtered (e.g., with a low-pass and/or band-pass filter) and digitized with an ADC to generate the raw data.

During step 1006, a range FFT is performed on the raw digital data $x_{out\_dig}(n)$ to generate range data. For example, in some embodiments, the raw digital data $x_{out\_dig}(n)$ are zero-padded and the fast Fourier transform (FFT) is applied to generate the range data. The range of skin surface 202a can be modeled by $R(\tau)$, where T represents the "slow-time."

Since, in some embodiments, the distance d between transmitting antenna 814 and skin surface 202a is fixed, the target bin $R_s$ (the range bin that includes information about deformations of skin surface 202a at location 210) may also be fixed. Thus, in some embodiments, the skin distension signal $d_s$ may be extracted from the unwrapped phase history $\psi(n)$ associated with the target range bin $R_s$. For example, in some embodiments, the FFT is performed over each row of a raw data matrix M based on raw digital data $x_{out\_dig}(n)$ and including a fast-time dimension and a slow-time dimension. The phase history is extracted from the column of matrix M associated with the target range bin $R_s$ and is unwrapped (e.g., adding or subtracting $2\pi$ for phase jumps larger than $-\pi$ or $+\pi$) to generate the unwrapped phase history $\psi(n)$ during step 1008. The skin distension signal $d_s(n)$ may be calculated by $$d_s(n) = \frac{\lambda \psi(n)}{4\pi} \qquad (13)$$

where $\lambda$ is the wavelength of the carrier frequency.

In some embodiments, the same millimeter-wave radar system (e.g., 800) used to generate the skin distension signal $d_s$ (e.g., during step 302) may be used to heat skin surface 202a (e.g., at location 210), e.g., during step 510. For example, the short wavelength radiation in the millimeter-wave regime limits the penetrations of the human body to predominately the skin surface 202a. Thus, increasing the power level of the radiation of radar signals 806 generated by transmitting antenna 814 may be used to increase the temperature of skin surface 202a while simultaneously being used by millimeter-wave radar system 800 to generate skin distension signal $d_s$.

FIG. 11A shows plot 1100 illustrating the progression over time of radiated RF energy from millimeter-wave radar system 800 (curve 1102) and peak skin distension $d_{s\_peak}$ (curve 1104), according to an embodiment of the present invention. FIG. 11B shows plot 1120 illustrating the progression over time of the temperature of skin surface 202a at location 210 (curve 1122) and peak skin distension $d_{s\_peak}$ (curve 1104), according to an embodiment of the present invention. Curve 1122 represents the temperature of skin surface 202a at location 210 corresponding to the cumulative RF energy radiated illustrated by curve 1102. FIGS. 11A and 11B may be understood together. Plots 100 and 1200 correspond to a constant systolic blood pressure $P_{SBP}$.

As shown in FIG. 11A, as a constant power is transmitted by transmitting antenna 814, the cumulative RF energy increases linearly, as shown by curve 1102. The temperature of the skin surface 202a at location 210 may also increase, e.g., proportionally, with respect to curve 1102, as shown by curve 1122. In some embodiments, the power transmitted by transmitting antenna 814 to cause an increase in temperature of skin surface 202a at location 210 may be between 50 mW and 500 mW.

As shown by curve 1104, as the temperature of skin surface 202a at location 210 increases, the peak skin distension $d_{s\_peak}$ at location 210 also increases. Thus, since peak skin distension $d_{s\_peak}$ is indicative of skin elasticity, changes in skin elasticity with respect to temperature can be estimated based on changes in peak skin distension $d_{s\_peak}$ with respect to temperature. In some embodiments, actual skin elasticity (e.g., as determined by a cutometer), may be correlated with peak skin distension $d_{s\_peak}$ so as to determine actual skin elasticity, e.g., with respect to temperature.

In some embodiments, millimeter-wave radar 802 applies energy to skin surface 202a at location 210 at a constant rate to cause an increase in temperature of skin surface 202a at location 210. In some embodiments, millimeter-wave radar 802 applies energy to skin surface 202a at location 210 linearly to cause an increase in temperature of skin surface 202a at location 210. In some embodiments, millimeter-wave radar 802 applies energy to skin surface 202a at location 210 non-linearly to cause an increase in temperature of skin surface 202a at location 210.

Figure 12A:
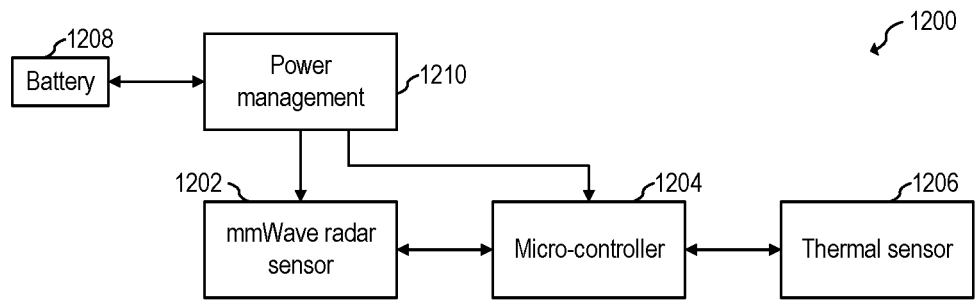
FIG. 12A shows a schematic diagram of a wearable device, according to an embodiment of the present invention.

FIG. 12A shows a schematic diagram of wearable device 1200, according to an embodiment of the present invention. Wearable device 1200 may be, e.g., a watch, writs band, fitness band, or any band designed to be worn in the wrist of a human.

Wearable device 1200 includes a (e.g., rechargeable) battery 1208, power management circuit 1210, millimeter-wave radar sensor 1202, micro-controller 1204, and thermal sensor 1206.

Power management circuit 1210 may include one or more power converters, such as LDOs and/or switched-mode power supplies for generating supply rails for one or more circuits of wearable device 1200, such as millimeter-wave radar sensor 1202 and micro-controller 1204. Power management circuit 1210 may be implemented in any way known in the art.

Micro-controller 1204 may be implemented, e.g., as a general purpose or custom micro-controller. Millimeter-wave radar sensor 1202 may be implemented as millimeter-wave radar sensor 802. Millimeter-wave radar sensor 1202 and micro-controller 1202 may implement millimeter-wave radar system 800.

Thermal sensor 1206 may be implemented with a thermistor or thermocouple. In some embodiments, thermal sensor 1206 may be implemented with an IR sensor. In some embodiments, thermal sensor 1206 includes a diode for determining the temperature. In some embodiments, the thermal sensor 1206 is implemented inside the millimeter-wave radar sensor 1202 IC or inside the micro-controller 1206 IC.

In some embodiments, thermal sensor 1206 determines the temperature of skin surface 202a (e.g., at location 210) by measuring the ambient temperature near location 210.

Figure 12B:
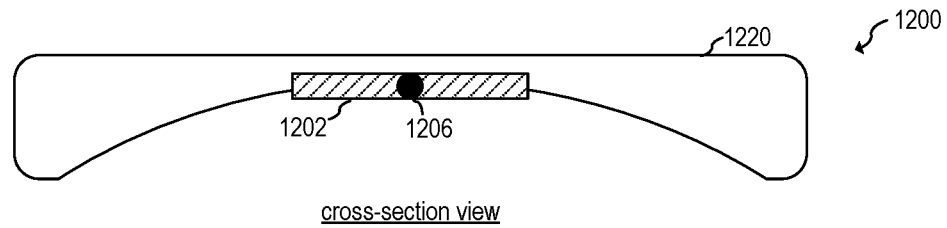
FIG. 12B shows a cross-section view of the wearable device of FIG. 12A, according to an embodiment of the present invention.

FIG. 12B shows a cross-section view of wearable device 1200, according to an embodiment of the present invention. As shown in FIG. 12B, enclosure 1220 includes thermal device 1206 disposed next to millimeter-wave radar sensor 1202 IC. Enclosure 1220 may also include battery 1208 (not shown), power management circuit 1210 (not shown), and micro-controller 1204 (not show).

Figure 12C:
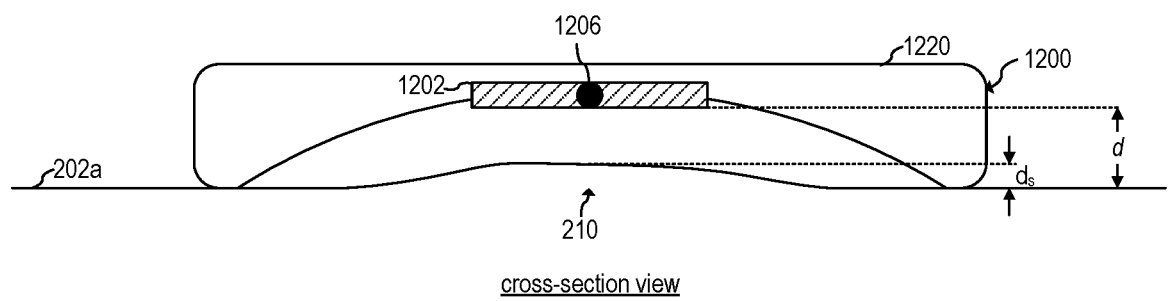
FIG. 12C shows the wearable device of FIGS. 12A and 12B disposed in a wrist of a human over the radial artery, according to an embodiment of the present invention.

FIG. 12C shows wearable device 1200 disposed in a wrist of a human over the radial artery, according to an embodiment of the present invention. As shown in FIG. 12C, wearable device 1200 measures skin distension and temperature at location 210 without contacting location 210. By avoiding contact with location 210, some embodiments, advantageously avoid disturbing the skin distension measurement, which may advantageously result in a more accurate blood pressure determination. Additionally, by not contacting millimeter-wave radar sensor 1202 with location 210, some embodiments are advantageously capable of maintaining a fixed distance d between transmitting antenna 814 and skin surface 202a reference, as skin surface 202a at location 210 moves, which may advantageously result in more accurate blood pressure determinations when the human is active, such as walking, or moving the arms or hands, for example.

Example embodiments of the present invention are summarized here. Other embodiments can also be understood from the entirety of the specification and the claims filed herein.

Example 1. A method including: generating a displacement signal indicative of a distension of a surface of a skin; determining a temperature of the skin using a temperature sensor; during a calibration time interval, collecting a plurality of distension values from the displacement signal, the plurality of distension values associated with a respective plurality of temperature values determined using the temperature sensor, the plurality of temperature values being indicative of a temperature change of the skin; determining compensation coefficients associated with the plurality of temperature values; and after the calibration time interval, collecting a first distension value from the displacement signal, determining a first temperature value using the temperature sensor, and determining a blood pressure based on the first distension value, the first temperature value, and the determined compensation coefficients.

Example 2. The method of example 1, further including, during the calibration time interval, applying energy to the skin or removing energy from the skin to cause a change in the temperature of the skin.

Example 3. The method of one of examples 1 or 2, where applying energy to the skin or removing energy from the skin includes applying or removing energy linearly with respect to time.

Example 4. The method of one of examples 1 to 3, where applying energy to the skin or removing energy from the skin includes applying or removing energy non-linearly with respect to time.

Example 5. The method of one of examples 1 to 4, further including, during the calibration time interval, applying electromagnetic waves to the skin to cause an increase in the temperature of the skin.

Example 6. The method of one of examples 1 to 5, where applying electromagnetic waves to the skin includes applying radar pulses to the skin using a millimeter-wave radar, the method further including using the millimeter-wave radar to generate the displacement signal.

Example 7. The method of one of examples 1 to 6, where generating the displacement signal includes generating the displacement signal using a radar.

Example 8. The method of one of examples 1 to 7, where the radar operates as a frequency-modulated continuous-wave (FMCW) radar in a frequency range including 60 GHz.

Example 9. The method of one of examples 1 to 7, where the radar operates as a frequency-modulated continuous-wave (FMCW) radar in a frequency range including 120 GHz.

Example 10. The method of one of examples 1 to 9, where generating the displacement signal includes generating the displacement signal using a capacitive sensor.

Example 11. The method of one of examples 1 to 10, where generating the displacement signal includes generating the displacement signal using a piezo-electric sensor attached to the surface of the skin.

Example 12. The method of one of examples 1 to 11, where determining the temperature of the skin includes determining the temperature of the surface of the skin using a thermistor.

Example 13. The method of one of examples 1 to 11, where determining the temperature of the skin includes using an infra-red (IR) sensor.

Example 14. The method of one of examples 1 to 13, where the temperature sensor includes a diode.

Example 15. The method of one of examples 1 to 14, where the surface of the skin includes a surface of a wrist of a human.

Example 16. The method of one of examples 1 to 15, where collecting the plurality of distension values includes storing the plurality of distension values in a volatile memory.

Example 17. The method of one of examples 1 to 16, where, during the calibration time interval, the displacement signal includes N displacement peaks, and where the plurality of distension values includes N distension values corresponding to the N displacement peaks.

Example 18. The method of one of examples 1 to 17, where the first distension value corresponds to an amplitude peak of the displacement signal.

Example 19. The method of one of examples 1 to 18, further including storing the compensation coefficients in a look-up table (LUT) addressable based on temperature values.

Example 20. The method of one of examples 1 to 19, further including determining an elasticity of the skin based on the plurality of distension values collected during the calibration time interval.

Example 21. The method of one of examples 1 to 20, where determining the blood pressure includes determining a systolic blood pressure value or a diastolic blood pressure value.

Example 22. A method including: transmitting a plurality of radar signals towards a surface of a skin using a millimeter-wave radar; receiving a plurality of reflected radar signals using the millimeter-wave radar; using the millimeter-wave radar, generating a displacement signal indicative of a distension of the surface of the skin based on the reflected radar signals, the skin covering a blood vessel; determining a temperature of the skin using a temperature sensor; during a calibration time interval, applying electromagnetic energy to the skin using the millimeter-wave radar to cause an increase in temperature of the skin, collecting a plurality of distension values from the displacement signal, the plurality of distension values associated with a respective plurality of temperature values determined using the temperature sensor, the plurality of temperature values indicative of the temperature increase of the skin caused by the applied electromagnetic energy, and determining compensation coefficients associated with the plurality of temperature values; and after the calibration time interval, collecting a first distension value from the displacement signal, determining a first temperature value using the temperature sensor, and determining a blood pressure based on the first distension value, the first temperature value, and the determined compensation coefficients.

Example 23. The method of example 22, where the blood vessel is the radial artery.

Example 24. A wearable device including: a millimeter-wave radar configured to: transmit a plurality of a plurality of radar signals towards a surface of a skin, receive a plurality of reflected radar signals, and generate a displacement signal indicative of a distension of the surface of the skin based on the reflected radar signals; a temperature sensor configured to measure temperature indicative of a temperature of the surface of the skin; and a controller configured to: during a calibration time interval, cause the millimeter-wave radar to apply electromagnetic energy to the skin to cause an increase in temperature of the skin, collect a plurality of distension values from the displacement signal, the plurality of distension values associated with a respective plurality of temperature values determined using the temperature sensor, the plurality of temperature values indicative of the temperature increase of the skin caused by the applied electromagnetic energy, and determine compensation coefficients associated with the plurality of temperature values, and after the calibration time interval, collect a first distension value from the displacement signal, determine a first temperature value using the temperature sensor, and determine a blood pressure based on the first distension value, the first temperature value, and the determined compensation coefficients.

Example 25. The wearable device of example 24, where the wearable device is a watch or fitness band.

Example 26. The wearable device of one of examples 24 or 25, where a distance between the millimeter-wave radar and the surface of the skin is fixed.

Example 27. The wearable device of one of examples 24 to 26, where the controller includes a local portion and a remote portion, and where the remote portion of the controller is configured to determine the blood pressure, and transmit the determined blood pressure to the local portion of the controller via the Internet.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A method comprising:
generating a displacement signal indicative of a distension of a surface of a skin;
determining temperature values indicative of measured temperatures of the skin using a temperature sensor;
during a calibration time interval,
collecting a plurality of distension values from the displacement signal, the plurality of distension values associated with a respective plurality of the temperature values determined using the temperature sensor, wherein the plurality of the temperature values are indicative of a temperature change of the skin, and
applying energy to the skin or removing energy from the skin to cause the temperature change of the skin;
determining compensation coefficients associated with the plurality of the temperature values; and
after the calibration time interval,
collecting a first distension value from the displacement signal, the first distension value associated with a respective first temperature value of the temperature values, wherein the first distension value is separate from the plurality of distension values, and the first temperature value is separate from the plurality of the temperature values, and determining a blood pressure based on the first distension value, the first temperature value, and the determined compensation coefficients.

2. The method of claim 1, wherein the applying energy to the skin or the removing energy from the skin comprises applying or removing energy linearly with respect to time.

3. The method of claim 2, wherein the applying energy to the skin or the removing energy from the skin comprises applying or removing energy non-linearly with respect to time.

4. The method of claim 2, wherein during the calibration time interval, the applying energy to the skin comprises applying electromagnetic waves to the skin to cause the temperature change of the skin, wherein the temperature change of the skin comprises an increase in the temperature of the skin.

5. The method of claim 4, wherein applying the electromagnetic waves to the skin comprises applying radar pulses to the skin using a millimeter-wave radar, the method further comprising using the millimeter-wave radar to generate the displacement signal.

6. The method of claim 1, wherein generating the displacement signal comprises generating the displacement signal using a radar.

7. The method of claim 6, wherein the radar operates as a frequency-modulated continuous-wave (FMCW) radar in a frequency range comprising 60 GHz.

8. The method of claim 6, wherein the radar operates as a frequency-modulated continuous-wave (FMCW) radar in a frequency range comprising 120 GHz.

9. The method of claim 1, wherein generating the displacement signal comprises generating the displacement signal using a capacitive sensor.

10. The method of claim 1, wherein generating the displacement signal comprises generating the displacement signal using a piezo-electric sensor attached to the surface of the skin.

11. The method of claim 1, wherein the temperature sensor comprises a thermistor.

12. The method of claim 1, wherein the temperature sensor comprises an infra-red (IR) sensor.

13. The method of claim 1, wherein the temperature sensor comprises a diode.

14. The method of claim 1, wherein the surface of the skin comprises a surface of a wrist of a human.

15. The method of claim 1, wherein collecting the plurality of distension values comprises storing the plurality of distension values in a volatile memory.

16. The method of claim 1, wherein, during the calibration time interval, the displacement signal comprises N displacement peaks, and wherein the plurality of distension values comprises N distension values corresponding to the N displacement peaks.

17. The method of claim 1, wherein the first distension value corresponds to an amplitude peak of the displacement signal.

18. The method of claim 1, further comprising storing the compensation coefficients in a look-up table (LUT) addressable based on the plurality of the temperature values.

19. The method of claim 1, further comprising determining an elasticity of the skin based on the plurality of distension values collected during the calibration time interval.

20. The method of claim 1, wherein determining the blood pressure comprises determining a systolic blood pressure value or a diastolic blood pressure value.

21. A method comprising:
transmitting a plurality of radar signals towards a surface of a skin using a millimeter-wave radar;
receiving a plurality of reflected radar signals using the millimeter-wave radar;
using the millimeter-wave radar, generating a displacement signal indicative of a distension of the surface of the skin based on the reflected radar signals, the skin covering a blood vessel;
determining temperature values indicative of measured temperatures of the skin using a temperature sensor;
during a calibration time interval,
applying electromagnetic energy to the skin via the transmitted plurality of radar signals using the millimeter-wave radar to cause an increase in the temperature of the skin,
collecting a plurality of distension values from the displacement signal, the plurality of distension values associated with a respective plurality of the temperature values determined using the temperature sensor, wherein the plurality of the temperature values are indicative of the increase in the temperature of the skin caused by the applied electromagnetic energy, and
determining compensation coefficients associated with the plurality of the temperature values; and
after the calibration time interval,
collecting a first distension value from the displacement signal, the first distension value associated with a respective first temperature value of the temperature values, wherein the first distension value is separate from the plurality of distension values, and the first temperature value is separate from the plurality of the temperature values, and
determining a blood pressure based on the first distension value, the first temperature value, and the determined compensation coefficients.

22. The method of claim 21, wherein the blood vessel is a radial artery.

23. A wearable device comprising:
a millimeter-wave radar configured to:
transmit a plurality of a plurality of radar signals towards a surface of a skin,
receive a plurality of reflected radar signals, and
generate a displacement signal indicative of a distension of the surface of the skin based on the reflected radar signals;
a temperature sensor configured to determine temperature values indicative of measured temperatures of the surface of the skin; and
a controller configured to:
during a calibration time interval,
cause the millimeter-wave radar to apply electromagnetic energy to the skin to cause an increase in temperature of the skin,
collect a plurality of distension values from the displacement signal, the plurality of distension values associated with a respective plurality of the temperature values determined using the temperature sensor, the plurality of the temperature values indicative of the temperature increase of the skin caused by the applied electromagnetic energy, and determine compensation coefficients associated with the plurality of the temperature values, and after the calibration time interval,
collect a first distension value from the displacement signal, the first distension value associated with a respective first temperature value of the temperature values, wherein the first distension value is separate from the plurality of distension values, and the first temperature value is separate from the plurality of the temperature values, determine a blood pressure based on the first distension value, the first temperature value, and the determined compensation coefficients.

24. The wearable device of claim 23, wherein the wearable device is a watch or fitness band.

25. The wearable device of claim 23, wherein a distance between the millimeter-wave radar and the surface of the skin is fixed.

26. The wearable device of claim 23, wherein the controller comprises a local portion and a remote portion, and wherein the remote portion of the controller is configured to determine the blood pressure, and transmit the determined blood pressure to the local portion of the controller via the Internet.

* * * * *